US006902886B1

(12) United States Patent
Citovsky et al.

(10) Patent No.: US 6,902,886 B1
(45) Date of Patent: Jun. 7, 2005

(54) GENETIC ASSAY FOR PROTEIN NUCLEAR TRANSPORT

(75) Inventors: Vitaly H. Citovsky, Commack, NY (US); Yoon Rhee, Coram, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/435,274

(22) Filed: Nov. 5, 1999

Related U.S. Application Data

(60) Provisional application No. 60/107,417, filed on Nov. 6, 1998.

(51) Int. Cl.[7] ........................ C12Q 1/68; C07K 14/195; C07H 21/04
(52) U.S. Cl. ........................ 435/6; 435/254.2; 435/325; 435/320.1; 536/23.1; 536/24.1; 530/350
(58) Field of Search ............................... 536/23.1, 24.1; 435/6, 320.1, 325, 254.2; 530/350

(56) References Cited

U.S. PATENT DOCUMENTS

| | | | |
|---|---|---|---|
| 5,137,822 A | * 8/1992 | Yabusaki et al. | ........... 435/193 |
| 5,283,173 A | 2/1994 | Fields et al. | ................. 435/6 |
| 5,525,490 A | 6/1996 | Erickson et al. | .............. 435/29 |
| 5,654,168 A | * 8/1997 | Bujard et al. | .............. 435/69.1 |
| 5,667,973 A | 9/1997 | Fields et al. | .................... 435/6 |
| 5,691,188 A | * 11/1997 | Pausch et al. | ........... 435/254.2 |

FOREIGN PATENT DOCUMENTS

| | | |
|---|---|---|
| WO | WO97/23609 | 7/1997 |
| WO | WO97/24457 | 7/1997 |
| WO | WO98/25947 | 6/1998 |
| WO | WO98/49284 | 11/1998 |
| WO | WO 98/49284 | * 11/1998 |

OTHER PUBLICATIONS

Geneseq database entry No. AAV70967, first entered Mar. 4, 1999.*
Geneseq database entry No. AAW85001, first entered Mar. 4, 1999.*
Ballas and Citovsky (1997) Proc Natl Acad Sci USA 94:10723–10728.
Bardwell et al. (1993) Med Microbiol 8:1177.
Bartel et al. (1993) Biotechniques 14:920.
Bogerd et al. (1993) J Virol 67:5030.
Chakraborty et al. (1992) J Biol Chem 267:17498.
Chien et al. (1991) Proc Natl Acad Sci USA 88:9578–9582.
Citovsky et al. (1992) Science 256:1803–1805.
Dasmahapatra et al. (1992) Proc Natl Acad Sci USA 89:4159.
Dingwall and Laskey (1991) Trends Biochem Sci 16:478–481.
Durfee et al. (1993) Genes Devel 7:555.
Fields and Song (1989) Nature 340:245.
Germino et al. (1993) Proc Natl Acad Sci USA 90:933.
Goldfarb et al. (1986) Nature 322:641–644.
Golemis and Brent (1992) Mol Cell Biol 12(7):3006–3014.
Guarente (1993) Proc Natl Acad Sci USA 90:1639.
Gulochon–Mantel et al. (1989) Cell 57:1147–1154.
Guralnick et al. (1996) Plant Cell 8:363–373.
Hardy et al. (1992) Genes Devel 6:801.
Hollenberg et al. (1995) Mol Cell Biol 15(7):3813–3822.
Iwabuchi et al. (1993) Oncogene 8:1693.
Jackson et al. (1993) Mol Cell Biol 13:2899.
Kalderon et al. (1984) Cell 39:499–509.
Lalo et al. (1993) Proc Natl Acad Sci USA 90:5524.
Li and Fields (1993) FASEB J 7:957.
Luban et al. (1993) Cell 73:1067.
Madura et al. (1993) J Biol Chem 268:12046.
Michael et al. (1995) Cell 83:415–422.
Milne and Weaver (1993) Genes Devel 7:1755.
Newmeyer et al. (1988) Cell 53:641–653.
Nigg (1997) Nature 386:779–787.
Ossareh–Nazari et al. (1997) Science 278:141–144.
Picard and Yamamoto (1987) EMBO J 6(11):3333–3340.
Robbins et al. (1991) Cell 64:615–623.
Roberts et al. (1987) Cell 50:465–475.
Schlenstedt et al. (1993) J Cell Biol 123:785–798.
Silver et al. (1986) Mol Cell Biol 6(12):4763–4766.
Silver and Hunt (1993) Mol Biol Rep 17:155.
Straudinger et al. (1993) J Biol Chem 268:4608.
Ueki et al. (1998) Nature Biotechnology 16(13):1338–1342.
Varagona et al. (1991) Plant Cell 3:105–113.
Vojtek et al. (1993) Cell 74:205.
Yang et al. (1992) Science 257:680.

* cited by examiner

*Primary Examiner*—James Ketter
*Assistant Examiner*—David A. Lambertson
(74) *Attorney, Agent, or Firm*—Rogalskyj & Weyand LLP

(57) ABSTRACT

The invention provides methods of determining the presence of a nuclear localization signal and/or the presence of a nuclear export signal in a protein of interest. The invention further provides chimeric nucleic acids and recombinant host cells for use in such methods. Additionally provided is a nucleic acid molecule encoding a modified LexA protein, wherein the modified LexA protein has no nuclear localization signal, as well as the modified LexA protein itself. In the nuclear import assay, if a protein of interest fused to a mLexA-Gal4AD hybrid contains a functional NLS, the fusion product will enter the yeast cell nucleus and activate the expression of reporter genes. In the nuclear export assay, if a protein of interest fused to a mLexA-SV40 NLS-Gal4AD hybrid contains a functional NES, the fusion product localized to the cell nucleus will exit into the cytoplasm, decreasing the reporter gene expression levels.

35 Claims, 19 Drawing Sheets

|  | | | | | | | | | | |
|---|---|---|---|---|---|---|---|---|---|---|
| WILD-TYPE LexA | (457) GTT | ACC | GTT | AAG | CGC | CTG | AAA | AAA | CAG | GGC | AAT (489) |
| | (153)  V  |  T  |  V  |  K  |  R  |  L  |  K  |  K  |  Q  |  G  |  N  (163) |
| | | | | | * | | * | | | | |
| MODIFIED LexA | (153)  V  |  T  |  V  |  K  |  G  |  L  |  E  |  K  |  Q  |  G  |  N  (163) |
| | (489) GTT | ACC | GTT | AAG | GGC | CTG | GAA | AAA | CAG | GGC | AAT (489) |
FIG. 17
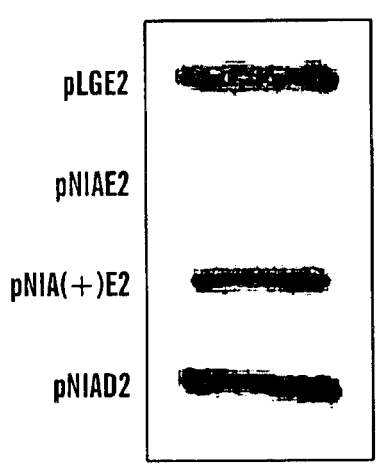
FIG. 18
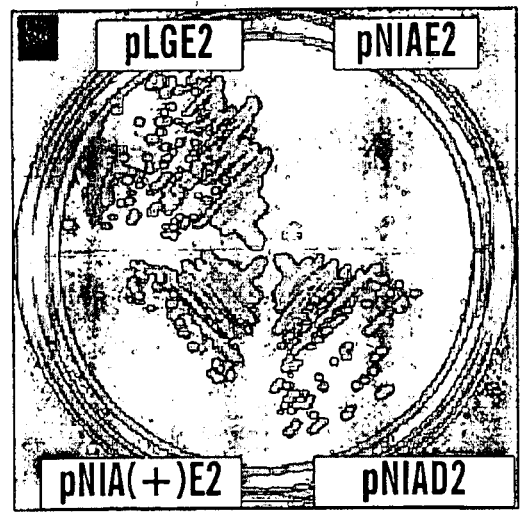
FIG. 19

SEQUENCE LISTING

```
<160> NUMBER OF SEQ ID NOS: 17

<210> SEQ ID NO 1
<211> LENGTH: 611
<212> TYPE: DNA
<213> ORGANISM: Unknown Organism
<220> FEATURE:
<223> OTHER INFORMATION: Description of Unknown Organism:bacterial
<223> OTHER INFORMATION: modified bacterial lexA

<400> SEQUENCE: 1
atgaaagcgt taacggccag gcaacaagag gtgtttgatc tcatccgtga tcacatcagc      60
cagacaggta tgccgccgac gcgtgcggaa atcgcgcagc gtttggggtt cgttcccccaa    120 acgcggctga agaacatctg aaggcgctgg cacgcaaagg cgttattgaa attgtttccg    180
gcgcatcacg cgggattcgt ctgttgcagg aagaggaaga agggttgccg ctggtaggtc    240
gtgtggctgc cggtgaacca cttctggcgc aacagcatat tgaaggtcat tatcaggtcg    300
atccttcctt attcaagccg aatgctgatt tcctgctgcg cgtcagcggg atgtcgatga    360
aagatatcgg cattatggat ggtgacttgc tggcagtgca taaaactcag gatgtacgta    420
acggtcaggt cgttgtcgca cgtattgatg acgaagttac cgttaagggc ctggaaaaac    480
agggcaataa agtcgaactg ttgccagaaa atagcgagtt taaaccaatt gtcgttgacc    540
ttcgtcagca gagcttcacc attgaagggc tggcggttgg ggttattcgc aacggcgact    600
ggctggaatt c                                                          611
```

<210> SEQ ID NO 2
<211> LENGTH: 204
<212> TYPE: PRT
<213> ORGANISM: Unknown Organism
<220> FEATURE:
<223> OTHER INFORMATION: Description of Unknown Organism:bacterial
<223> OTHER INFORMATION: modified bacterial lexA

<400> SEQUENCE: 2

Met Lys Ala Leu Thr Ala Arg Gln Gln Glu Val Phe Asp Leu Ile Arg
 1               5                  10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
 65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Gly Leu Glu Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe
        195                 200

<210> SEQ ID NO 3
<211> LENGTH: 7
<212> TYPE: PRT
<213> ORGANISM: Simian virus 40
<220> FEATURE:
<223> OTHER INFORMATION: large T antigen NLS

<400> SEQUENCE: 3

Pro Lys Lys Lys Arg Lys Val
 1               5

<210> SEQ ID NO 4
<211> LENGTH: 17
<212> TYPE: PRT
<213> ORGANISM: Xenopus sp.
<220> FEATURE:
<223> OTHER INFORMATION: nucleoplasmin NLS
<221> NAME/KEY: VARIANT
<222> LOCATION: (3)..(13)
<223> OTHER INFORMATION: Residues 3 to 13 in Xenopus laevis are Pro Ala
      Ala Thr Lys Lys Ala Gly Gln Ala Lys

<400> SEQUENCE: 4

Lys Arg Xaa Xaa Xaa Xaa Xaa Xaa Xaa Xaa Xaa Xaa Xaa Lys Lys Lys
 1               5                  10                  15

Leu

<210> SEQ ID NO 5
<211> LENGTH: 9
<212> TYPE: PRT
<213> ORGANISM: Human immunodeficiency virus type 1
<220> FEATURE:
<223> OTHER INFORMATION: Rev protein NES

<400> SEQUENCE: 5

Leu Pro Pro Leu Glu Arg Leu Thr Leu
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:nuclear
      export signal
<223> OTHER INFORMATION: mutated NES of pNEAM10

<400> SEQUENCE: 6

Leu Pro Pro Asp Leu Arg Leu Thr Leu
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:nuclear
      export signal
<223> OTHER INFORMATION: residual NES of pNEARev(delta)3

<400> SEQUENCE: 7

Leu Pro Pro Leu
 1

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:primer
      sequence
<223> OTHER INFORMATION: GAL4 primer

<400> SEQUENCE: 8
gggaattcaa ttttaatcaa agtggg                                    26

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:primer
      sequence
<223> OTHER INFORMATION: GAL4 primer

<400> SEQUENCE: 9
gacggatccc cgggtattcg atctctt                                   27

<210> SEQ ID NO 10
<211> LENGTH: 29
<212> TYPE: DNA
<213> ORGANISM: Artificial Sequence

```
<220> FEATURE:
<223> OTHER INFORMATION: Description of Artificial Sequence:primer
      sequence
<223> OTHER INFORMATION: GAL4 primer

<400> SEQUENCE: 10
gggaattcga taaagcggaa ttaattccc                                    29

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:primer
      sequence
<223> OTHER INFORMATION: GAL4 primer

<400> SEQUENCE: 11
gacggatccc cgggtattcg atctctt                                      27

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:primer
      sequence
<223> OTHER INFORMATION: mutant lexA primer

<400> SEQUENCE: 12
ccgttaaggg cctggaaaaa caggg                                        25

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:primer
      sequence
<223> OTHER INFORMATION: selection lexA primer

<400> SEQUENCE: 13
gtgactggtg aggcctcaac caagtc                                       26

<210> SEQ ID NO 14
<211> LENGTH: 33
<212> TYPE: DNA
<213> ORGANISM: Escherichia coli

<400> SEQUENCE: 14
gttaccgtta agcgcctgaa aaaacagggc aat                               33

<210> SEQ ID NO 15
<211> LENGTH: 11
<212> TYPE: PRT
<213> ORGANISM: Escherichia coli

<400> SEQUENCE: 15

Val Thr Val Lys Arg Leu Lys Lys Gln Gly Asn
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence:MODIFIED
```

```
                    BACTERIAL LEX A

<400> SEQUENCE: 16

Val Thr Val Lys Gly Leu Glu Lys Gln Gly Asn
  1               5                  10

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence:MODIFIED
      BACTERIAL LEX A

<400> SEQUENCE: 17
gttaccgtta agggcctgga aaaacagggc aat                               33
```

US 6,902,886 B1

GENETIC ASSAY FOR PROTEIN NUCLEAR TRANSPORT

This application claims priority of U.S. Provisional Patent Application No. 60/107,417, filed Nov. 6, 1998.

The subject matter of this application was made with support from the United States Government under National Institutes of Health Grant No. GM50224 and USDA Grant No. 9402564. The U.S. Government may have certain rights in this invention.

FIELD OF THE INVENTION

The subject invention is directed generally to a genetic assay, and more particularly to a genetic assay for protein nuclear transport, including nuclear import and nuclear export.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Nucleo-cytoplasmic shuttling of protein molecules is a basic biological process central to the regulation of gene expression (which underlies all aspects of development, morphogenesis, and signaling pathways in eukaryotic organisms). Furthermore, transport of proteins and protein-nucleic acid complexes in and out of the nucleus is an essential step in many host-pathogen interactions such as viral and bacterial infection. Nuclear traffic occurs exclusively through the nuclear pore complex (NPC). While small molecules (up to 40–60 kDa) diffuse through the NPC, nuclear import of larger molecules is mediated by specific Nuclear Localization Signal (NLS) sequences contained in the transported molecule (Garcia-Bustos et al. 1991; Dingwall 1991). Most NLSs can be classified in three general groups: (i) a monopartite NLS exemplified by the SV40 large T antigen NLS (SEQ ID NO:3: PKKKRKV); (ii) a bipartite motif consisting of two basic domains separated by a variable number of spacer amino acids and exemplified by the *Xenopus* nucleoplasmin NLS (SEQ ID NO:4: KRXXXXXXXXXXKKKL); and (iii) noncanonical sequences such as M9 of the hnRNP Al protein, the influenza virus nucleoprotein NLS, and the yeast Gal4 protein NLS (Dingwall and Laskey 1991).

Once in the nucleus, many proteins are transported back to the cytoplasm as an essential step in their biological function. For example, the Rev protein of human immunodeficiency virus type 1 (HIV-1): exits the nucleus, facilitating export of the unspliced viral RNA (Pollard and Malim 1998). Rev nuclear export is mediated by a specific Nuclear Export Signal (NES) consisting of the leucine-rich sequence, SEQ ID NO:5: LPPLERLTL, found also in proteins of other viruses (Dobbelstein et al. 1997). Also, numerous cellular proteins, such as I-KB and MAPKK, contain potential NES sequences which may regulate the biological activity of these proteins by controlling their nuclear export (Ullman et al. 1997).

The relatively small size of the NLS and NES sequences and, more importantly, the lack of clear and consistent consensus motifs in these signals, make it difficult to predict their presence in a given protein based solely on the analysis of its amino acid sequence. Furthermore, even if a consensus NLS or NES were found, it may not represent a functional signal. For example, β-glucuronidase (GUS), a commonly-used reporter enzyme which resides exclusively in the cell cytoplasm (Varagona et al. 1991; Citovsky et al. 1992), carries a perfect, albeit non-functional, bipartite NLS at its carboxy terminus. Thus, the only practical way to identify active NLS or NES signals is by microinjecting (Guralnick et al. 1996; Goldfarb et al. 1986; Kalderon et al. 1984) or expressing the protein of interest in eukaryotic cells (Varagona et al. 1991; Citovsky et al. 1992; Robbins et al. 1991; Roberts et al. 1987), heterokaryon formation (Michael et al. 1995), or using an in vitro transport system (Ossareh-Nazari et al. 1997; Schlenstedt et al. 1993; Newmeyer et al. 1988; Ballas and Citovsky 1997). Two major experimental approaches have been developed in this regard. In one approach, the protein of interest is labeled, microinjected into eukaryotic cells, and its intracellular localization determined. In another approach, the tested genes are fused to a reporter (β-galactosidase, green fluorescent protein, etc.), expressed in eukaryotic cells, and the localization of the resulting fusion protein determined. Both methods have serious technical disadvantages. The first approach is very labor-intensive and requires highly trained personnel experienced in protein purification, microinjection, and fluorescent or electron microscopy techniques. The second method is also very laborious, involving often elaborate procedures for genetic transformation of higher eukaryotic cells and microscopy observations. Since both of these procedures rely on physical intracellular localization of the protein, common artifacts such as perinuclear binding can present problems in analysis of results.

A need continues to exist, therefore, for a method for determining whether newly-cloned genes may encode a protein that localizes to or is exported from the cell nucleus.

SUMMARY OF THE INVENTION

The subject invention addresses this need by methods and compositions for determining the presence of a nuclear localization signal or a nuclear export signal in a protein of interest.

In regard to the nuclear localization signal, the invention provides a method of determining the presence of a nuclear localization signal in a protein of interest. The method comprises: selecting a host cell for use in the method, wherein the host cell contains a nucleus having nucleic acid encoding a reporter gene therein and wherein the host cell has a first level of expression of the reporter gene; identifying a DNA binding domain and an activation domain for the reporter gene; constructing a chimeric nucleic acid encoding a fusion protein comprising the DNA binding domain, the activation domain, and a protein of interest, wherein elements of the fusion protein other than the protein of interest have no nuclear localization signals; introducing the chimeric nucleic acid into the host cell; and determining a second level of expression of the reporter gene to determine the presence of a nuclear localization signal in the protein of interest.

The invention further provides a recombinant host cell comprising: a nucleus having nucleic acid encoding a reporter gene therein; and a chimeric nucleic acid encoding a fusion protein, the fusion protein comprising a DNA binding domain for the reporter gene, an activation domain for the reporter gene, and a protein of interest, wherein elements of the fusion protein other than the protein of interest have no nuclear localization signals.

Further provided is a chimeric nucleic acid encoding a fusion protein, the fusion protein comprising a DNA binding domain for a reporter gene, an activation domain for the reporter gene, and a protein of interest, wherein elements of the fusion protein other than the protein of interest have no nuclear localization signals. A vector comprising the chimeric nucleic acid molecule, as well as a kit comprising the vector, are also provided.

Additionally provided is a nucleic acid molecule encoding a modified LexA protein, wherein the modified LexA protein has no nuclear localization signal, as well as a modified LexA protein, wherein the modified LexA protein has no nuclear localization signal.

In regard to the nuclear export signal, the invention provides a method of determining the presence of a nuclear export signal in a protein of interest. The method comprises: selecting host cells for use in the method, wherein each of the host cells contain a nucleus having nucleic acid encoding a reporter gene therein; identifying a DNA binding domain and an activation domain for the reporter gene; constructing a chimeric nucleic acid encoding a fusion protein comprising the DNA binding domain, the activation domain, and a nuclear localization signal, wherein elements of the fusion protein have no nuclear export signals; introducing the chimeric nucleic acid into one of the host cells; determining a first level of expression of the reporter gene; constructing a second chimeric nucleic acid encoding a second fusion protein comprising the DNA binding domain, the activation domain, the nuclear localization signal, and a protein of interest; introducing the second chimeric nucleic acid into another one of the host cells; and determining a second level of expression of the reporter gene to determine the presence of a nuclear export signal in the protein of interest.

The invention further provides a recombinant host cell comprising: a nucleus having nucleic acid encoding a reporter gene therein; and a chimeric nucleic acid encoding a fusion protein, the fusion protein comprising a DNA binding domain for the reporter gene, an activation domain for the reporter gene, and a nuclear localization signal, wherein elements of the fusion protein have no nuclear export signals.

Further provided is a chimeric nucleic acid encoding a fusion protein, the fusion protein comprising a DNA binding domain for a reporter gene, an activation domain for the reporter gene, and a nuclear localization signal, wherein elements of the fusion protein have no nuclear export signals. A vector comprising the chimeric nucleic acid molecule, as well as a kit comprising the vector, are also provided.

More particularly, the invention provides a simple functional assay for protein nuclear import and export which circumvents all of the above mentioned difficulties. This assay has been used to demonstrate the nuclear import and export activities of a capsid protein (CP) from a plant *geminivirus*, suggesting a role for CP in nuclear shuttling of viral genomes during the infection process. The simple genetic system is used to detect active nuclear import (NLS) and export targeting signals (NES) based on their function within yeast cells. To generate one embodiment of this system, a gene encoding the bacterial LexA protein was modified (mLexA) to abolish its intrinsic nuclear targeting activity and fused to a sequence coding for the activation domain of the yeast Gal4 protein (Gal4AD) in the absence or presence of the SV40 large T-antigen NLS. In the nuclear import assay, if a protein of interest fused to the mLexA-Gal4AD hybrid contains a functional NLS, the fusion product will enter the yeast cell nucleus and activate the expression of reporter genes. In the nuclear export assay, if a protein of interest fused to the mLexA-SV40 NLS-Gal4AD hybrid contains a functional NES, the fusion product localized to the cell nucleus will exit into the cytoplasm, decreasing the reporter gene expression levels. This system was tested using proteins with known NLS and NES sequences and then the system was utilized to identify an NES within the capsid protein of a plant *geminivirus*. The results indicate that this system is applicable as a general method to identify and quantitatively analyze functional NLS and NES as well as to specifically select for proteins containing these signals.

BRIEF DESCRIPTION OF THE DRAWINGS

These and other features and advantages of this invention will be evident from the following detailed description of preferred embodiments when read in conjunction with the accompanying drawings in which:

FIG. 17 illustrates the wild type LexA NLS (nucleic acid sequence SEQ ID NO:14: amino acid sequence SEQ ID NO:15) and the modified LexA NLS (nucleic acid sequence SEQ ID NO:16; amino acid sequence SEQ ID NO:17);

FIG. 18 illustrates the results of a β-galactosidase assay used to detect nuclear import of a tested protein;

FIG. 19 illustrates the results of the selective reporter gene (HIS3) used to detect nuclear import of a tested protein (medium deficient for both tryptophan and histidine);

DETAILED DESCRIPTION OF THE INVENTION

Figure 1:
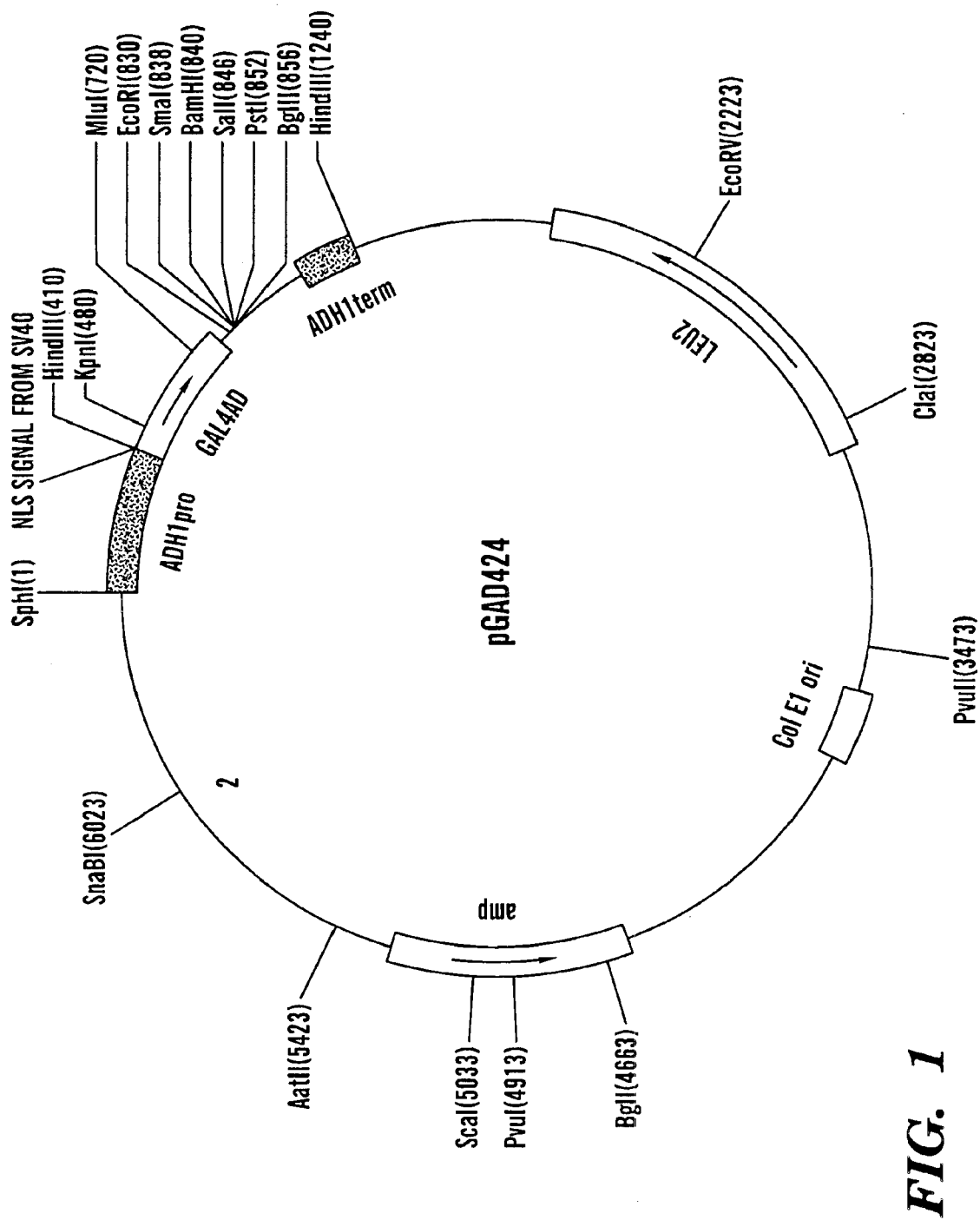
FIG. 1 is a map of pGAD424.

Abbreviations: PCR, polymerase chain reaction; mLexA, modified LexA; NIA, nuclear import assay; NEA, nuclear export assay; Gal4AD, Gal4 activation domain; HIV, human immunodeficiency virus; NLS, nuclear localization signal; NES, nuclear export signal; ORF, open reading frame; TYLCV, tomato yellow leaf curl virus; 3AT, 3-amino-1,2,4-triazole.

The subject invention provides a method of determining the presence of a nuclear localization signal in a protein of interest. The method comprises: selecting a host cell for use in the method, wherein the host cell contains a nucleus having nucleic acid encoding a reporter gene therein and wherein the host cell has a first level of expression of the reporter gene; identifying a DNA binding domain and an activation domain for the reporter gene; constructing a chimeric nucleic acid encoding a fusion protein comprising the DNA binding domain, the activation domain, and a protein of interest, wherein elements of the fusion protein other than the protein of interest have no nuclear localization signals; introducing the chimeric nucleic acid into the host cell; and determining a second level of expression of the reporter gene to determine the presence of a nuclear localization signal in the protein of interest.

The invention further provides a recombinant host cell comprising: a nucleus having nucleic acid encoding a reporter gene therein; and a chimeric nucleic acid encoding a fusion protein, the fusion protein comprising a DNA binding domain for the reporter gene, an activation domain for the reporter gene, and a protein of interest, wherein elements of the fusion protein other than the protein of interest have no nuclear localization signals.

Further provided is a chimeric nucleic acid encoding a fusion protein, the fusion protein comprising a DNA binding domain for a reporter gene, an activation domain for the reporter gene, and a protein of interest, wherein elements of the fusion protein other than the protein of interest have no nuclear localization signals. A vector comprising the chimeric nucleic acid is also provided.

Additionally provided is a nucleic acid molecule encoding a "modified" LexA protein which does not have a nuclear localization signal. In a presently preferred embodiment, the nucleic acid molecule encodes an amino acid sequence as shown in SEQ ID NO:2. SEQ ID NO:2 represents the amino acid sequence of the naturally-occurring LexA protein but with substitutions R157G and K159E. These amino acid substitutions prevent the nuclear localization signal normally present in the LexA protein from functioning properly. Therefore, the "modified" LexA protein having amino acid SEQ ID NO:2 has no nuclear localization signal (i.e. no functional nuclear localization signal) and cannot enter the nucleus on its own. In one preferred embodiment, the nucleic acid molecule encoding the "modified" LexA protein has a nucleotide sequence as shown in SEQ ID NO:1. SEQ ID NO:1 represents the nucleotide sequence of the naturally-occurring LexA protein but with the codons for amino acid residues 157 and 159 changed from CGC and AAA to GGC and GAA, respectively. These nucleotide substitutions alter the amino acid sequence of the LexA protein such that the nuclear localization signal normally present in the LexA protein does not function properly.

The invention further provides a "modified" LexA protein (mutated or modified from its naturally occurring amino acid and/or nucleotide sequence), wherein the modified LexA protein has no nuclear localization signal but maintains its ability to bind promoter elements. As discussed above, in a presently preferred embodiment the "modified" LexA protein has an amino acid sequence as shown in SEQ ID NO:2.

Also provided is a method of determining the presence of a nuclear export signal in a protein of interest. The method comprises: selecting host cells for use in the method, wherein each of the host cells contain a nucleus having nucleic acid encoding a reporter gene therein; identifying a DNA binding domain and an activation domain for the reporter gene; constructing a chimeric nucleic acid encoding a fusion protein comprising the DNA binding domain, the activation domain, and a nuclear localization signal, wherein elements of the fusion protein have no nuclear export signals; introducing the chimeric nucleic acid into one of the host cells; determining a first level of expression of the reporter gene; constructing a second chimeric nucleic acid encoding a second fusion protein comprising the DNA binding domain, the activation domain, the nuclear localization signal, and a protein of interest; introducing the second chimeric nucleic acid into another one of the host cells; and determining a second level of expression of the reporter gene to determine the presence of a nuclear export signal in the protein of interest.

The invention further provides a recombinant host cell comprising: a nucleus having nucleic acid encoding a reporter gene therein; and a chimeric nucleic acid encoding a fusion protein, the fusion protein comprising a DNA binding domain for the reporter gene, an activation domain for the reporter gene, and a nuclear localization signal, wherein elements of the fusion protein have no nuclear export signals.

Further provided is a chimeric nucleic acid encoding a fusion protein, the fusion protein comprising a DNA binding domain for a reporter gene, an activation domain for the reporter gene, and a nuclear localization signal, wherein elements of the fusion protein have no nuclear export signals. A vector comprising the chimeric nucleic acid molecule, as well as a kit comprising the vector, are also provided.

As used herein, "naturally occurring" as applied to an object refers to the fact that the object can be found in nature. For example, a protein that is present in an organism that can be isolated from that organism and which has not been intentionally modified by man in the laboratory is "naturally occurring".

As further used herein, a "nuclear localization signal" refers to an intrinsic signal in a protein or molecule that mediates active transport of the protein or molecule across nuclear pore complexes into the nucleus. As further used herein, a "nuclear export signal" refers to an intrinsic signal in a protein or molecule that mediates active transport of the protein or molecule across nuclear pore complexes out of the nucleus.

A "protein of interest" is intended to refer to any protein for which one wishes to determine whether such protein has a nuclear localization signal and/or a nuclear export signal.

Figure 10:
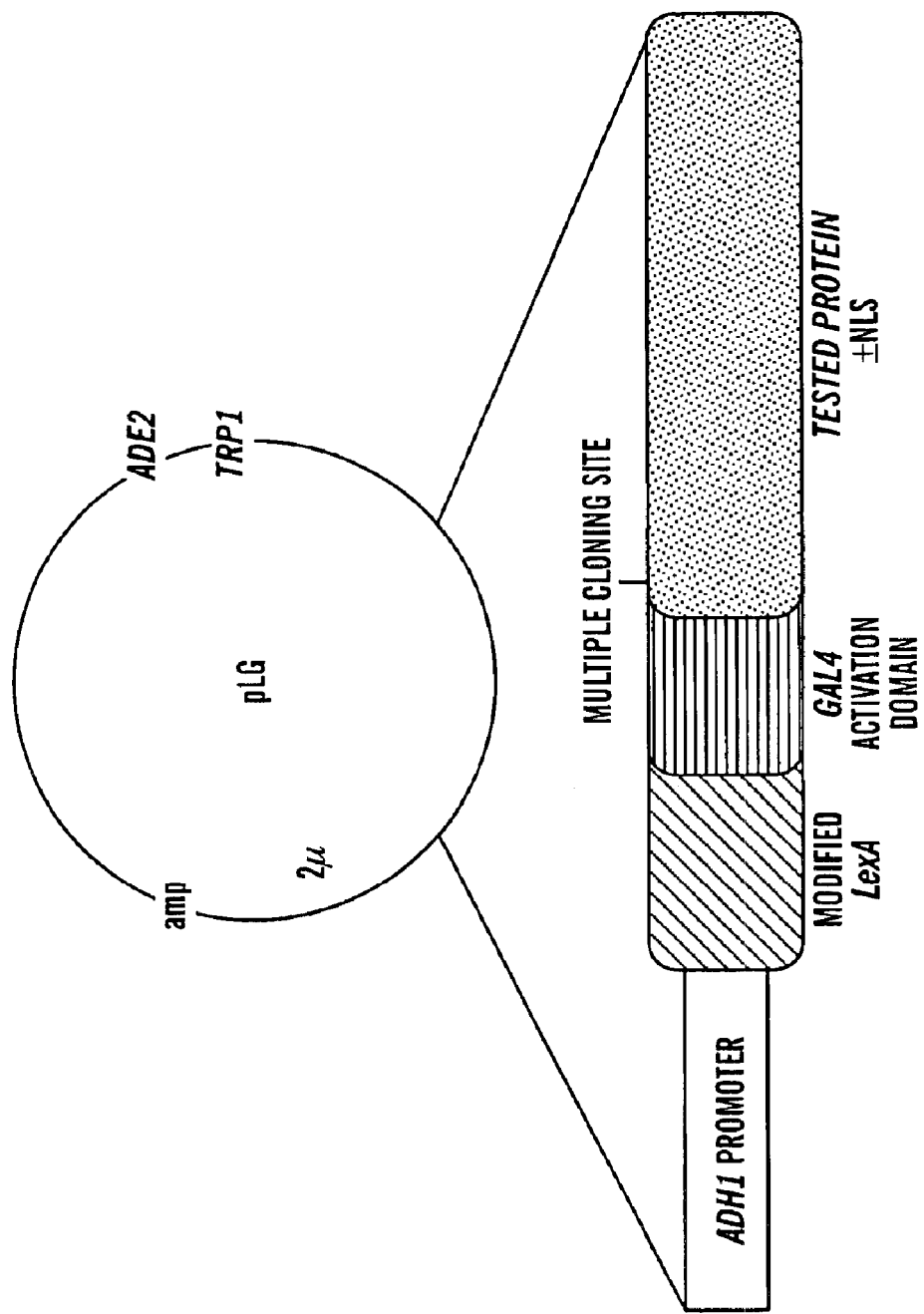
FIG. 10 is a map of pLG, showing the fusion protein construct used for the one-hybrid protein nuclear import assay.

With this general understanding of the terms used herein, the invention in regard to nuclear import provides an expression vector comprising a chimeric nucleic acid molecule (the chimeric nucleic acid molecule is described above as encoding a fusion protein, the fusion protein comprising a DNA binding domain for a reporter gene, an activation domain for the reporter gene, and a protein of interest, wherein elements of the fusion protein other than the protein of interest have no nuclear localization signal). In a presently preferred embodiment, the expression vector is a yeast one-hybrid expression vector, designated pLG, which was designed to conveniently and rapidly assay the ability of proteins to enter the cell nucleus. pLG expresses a triple-fusion protein comprising a modified bacterial LexA (the DNA binding domain), yeast Gal4 activation domain, and the tested protein encoded by a cDNA subcloned in-frame into the multiple cloning site downstream of Gal4 activation domain open reading frame (ORF) (FIG. 10).

Figure 11:
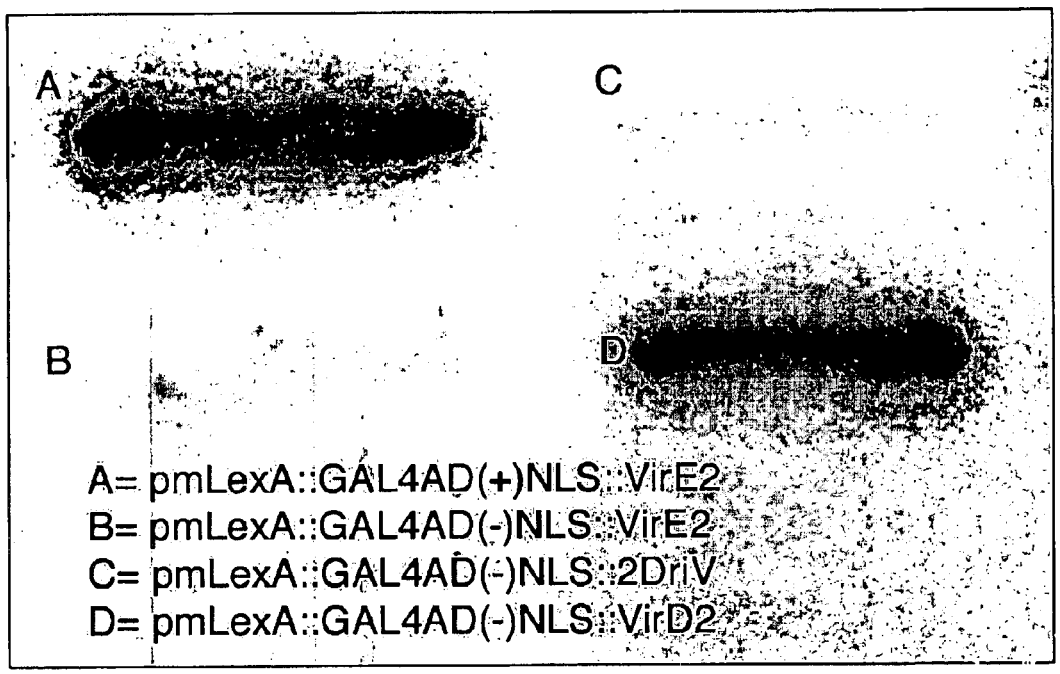
FIG. 11 illustrates the results of the β-galactosidase assay used to detect nuclear import of a tested protein.

When this expression vector is introduced into a host cell (having a nucleus having nucleic acid encoding the reporter gene therein), if the tested protein contains a functional nuclear localization signal (NLS), the fusion protein will enter the host cell nucleus. A presently preferred host cell for use with the pLG vector is the yeast L40 host cell, which contains a LacZ gene and a HIS3 gene. Following nuclear import (if the protein of interest includes a nuclear localization signal), the LexA domain targets the fusion protein to the LexA operator sites of the reporter lacZ gene contained in the L40 yeast strain. The Gal4 activation domain then activates the expression of lacZ resulting in β-galactosidase activity. In the absence of NLS, the fusion construct is unable to reach the cell nucleus and, thus, is unable to activate the reporter gene. Indeed, expression of pLG carrying a cDNA for a non-nuclear protein does not produce any detectable β-galactosidase activity (FIGS. 11 and 18).

Figure 12:
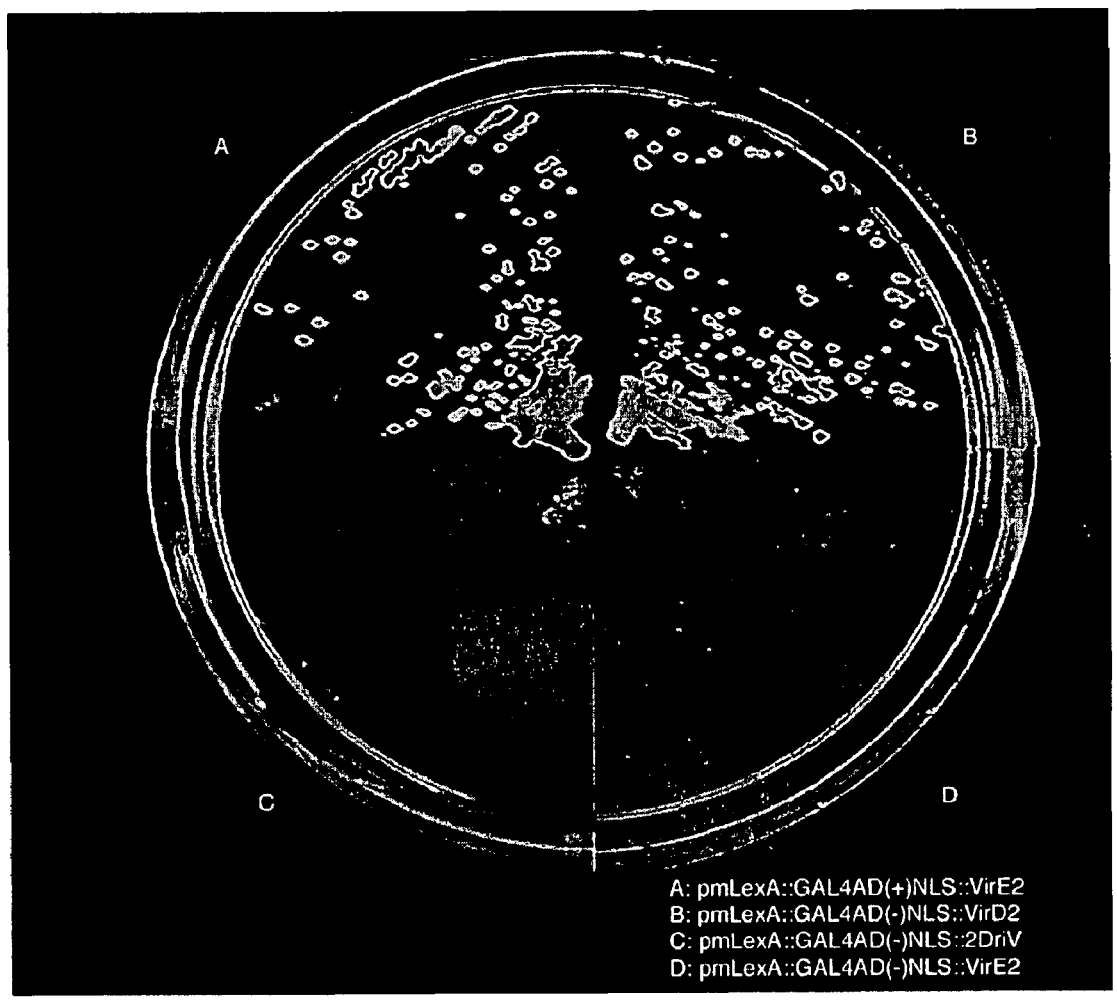
FIG. 12 illustrates the results of the selective reporter gene (HIS3) used to detect nuclear import of a tested protein.

In addition to induction of the β-galactosidase reporter, this one-hybrid system allows one to directly select for the nuclear import of the tested protein in the same L40 yeast strain, which contains an integrated copy of the HIS3 gene with upstream LexA operators. Similarly to the β-galactosidase expression, only cells expressing the NLS-containing fusion protein are able to grow on a histidine-deficient medium (FIGS. 12 and 19).

It should be apparent that because nuclear transport machinery is generally well conserved between different organisms (Nigg 1997), the import and export signals identified in accordance with the subject invention will likely be active in other eukaryotic cell types (and therefore host cells other than yeast can be used in the methods and compositions of the subject invention).

A component of the pLG vector is a modified LexA gene (see above discussion). Clearly, the success of the nuclear import assay using this vector hinges on the inability of LexA::Gal4::tested protein fusions to enter the cell nucleus in the absence of an NLS. Thus, neither LexA nor Gal4 should contain NLS sequences. Indeed, the Gal4 activation domain is known to lack NLS whereas LexA, a bacterial protein, was generally thought not to have evolved such a signal. However, the subject invention relies on the discovery that wild-type LexA carries a previously unidentified NLS sequence, rendering the above described experimental design impossible. To circumvent this difficulty, the LexA NLS was identified and inactivated by specific substitutions of two amino acid residues. This modification of LexA, or another modification to inactivate the NLS, is critical if the vector is constructed with LexA as the DNA binding domain. However, other DNA binding domains could be chosen that do not contain a nuclear localization signal to begin with.

pLG and L40 can be provided as a kit for simple and rapid functional assay of nuclear import. In addition, the kit should contain a positive control for nuclear import. A presently preferred positive control is a pLG derivative containing the SV40 NLS sequence at the LexA:Gal4 junction. Fusion proteins produced from this construct always localize to the nucleus, resulting in lacZ expression and cell growth in the absence of histidine. This control construct, therefore, is designed to demonstrate the functionality of the assay as well as the active conformation of the fusion protein.

It should be readily apparent to one of ordinary skill in the art that various elements of the expression vector and the selection of a particular host cell in which to conduct the assay for protein nuclear import can be varied. For example, in the plasmid pLG: the fusion protein is under regulatory control of the ADH1 promoter (see FIG. 10). The selection of a strong promoter to control expression of the fusion protein in the host cell is beneficial to distinguish expression of the fusion protein (and therefore nuclear import of the fusion protein) in the event that the reporter gene is otherwise activated within the host cell. A strong constitutive promoter such as ADH1 can be used, or a strong inducible promoter such as the GAL promoter may be used. In either case, the host cell can be expressing a first level of reporter gene product (for example, lacZ detectable by β-galactosidase) before introduction of the expression vector comprising the protein to be tested for nuclear import. Before the expression vector is introduced into the host cell in the case of a constitutive promoter, or after the expression vector is introduced into the host cell in the case of an inducible promoter, the first level can be determined (for the inducible promoter, the first level is after introduction but before induction). An increase in expression of the reporter gene product after introduction and/or induction indicates that the fusion protein entered the host cell nucleus. If the expression of the reporter gene cannot be quantitated to reveal whether the level of expression of the gene has increased, then the reporter gene must only be activated by the fusion protein construct of the subject invention and not by any other elements within the host cell. In this case, expression of the reporter gene in a qualitative sense indicates the presence of a nuclear localization signal in the tested protein. In the event that the DNA binding domain and the activation domain "down" regulate the reporter gene, decreased levels of expression would be screened for.

This could be the case where the DNA binding domain and the activation domain indirectly affect expression of the reporter gene, such as through a relay gene that represses expression of the reporter gene. This concept is discussed more fully in U.S. Pat. No. 5,525,490, the contents of which are incorporated herein by reference. As an example, the DNA binding domain and activation domain could turn on the Gal8O gene which then represses Gal4 and therefore HIS3 or lacZ. As another example, consider the lac operon which includes lacZ. CAP induces expression of the lac operon and therefore lacZ, while the lac repressor represses expression of the lac operon and therefore lacZ. Positive and negative regulation of the reporter gene of the subject invention, and direct and indirect (such as through Gal80) regulation of the reporter gene are specifically intended to be covered herein by the language regarding a DNA binding domain and an activation domain for a reporter gene. One thus compares the first and second levels of expression of the reporter gene to determine whether a nuclear import signal is present. If the nuclear binding domain and activation domain lead, directly or indirectly, to up-regulation of the reporter gene, then an increase in reporter gene expression signifies a nuclear localization signal. If the nuclear binding domain and activation domain lead, directly or indirectly, to down-regulation of the reporter gene, then a decrease in reporter gene expression signifies a nuclear localization signal.

Examples of suitable alternative constitutive promoters include yeast promoters (such as PGK, GAP, and TPI) and mammalian promoters (such as CMV), and examples of suitable alternative inducible promoters include yeast promoters (GAL1, GAL10, methionine) and mammalian promoters (glucocorticoid inducible promoter and estradiol inducible promoter).

The DNA binding domain and the activation domain for the chosen reporter gene can also be varied, as can the chosen reporter gene. The key is that the DNA binding domain recognizes and the gene activation domain activates, directly or indirectly, the same reporter gene). Importantly, the selection of a DNA binding domain and activation domain must ensure that they do not contain functional NLS sequences. As with LexA, if a DNA binding domain or activation domain is chosen which includes an NLS, the NLS can be modified to eliminate the nuclear localization signal function.

The combination of these two structural domains (the DNA binding domain and the activation domain) is generally referred to as a transcription activator. Transcription activators are proteins that generally positively regulate the expression of specific genes. As indicated, they can be functionally dissected into two structural domains: one region that binds to specific DNA sequences and thereby confers specificity, and another region termed the activation domain that binds to protein components of the basal gene expression machinery (Ma and Ptashne (1988)). These two domains need to be physically connected in order to function as a transcriptional activator. The host cell is chosen such that the transcriptional activator drives the expression of a specific reporter gene (such as HIS3 or lacZ), which provides the read-out for the nuclear import.

Examples of transcription activators include GAL4 and VP16, and examples of reporter genes include lacZ, CAT, luciferase, and GFP. The knowledge of two structural domains of transcription activators, and the knowledge that each domain must be present to activate a gene, has been utilized in yeast two-hybrid methodologies. For discussions of yeast two hybrid procedures generally, see Fields and Song (1989); Chein et al. (1991); Silver and Hunt (1993); Durfee et al. (1993); Yang et al. (1992); Luban et al. (1993); Hardy et al. (1992); Bartel et al. (1993); Vojtek et al. (1993); Li and Fields (1993); Lalo et al. (1993); Jackson et al. (1993); Madura et al. (1993); Bardwell et al. (1993); Chakraborty et al. (1992); Straudinger et al. (1993); Milne and Weaver (1993); Iwabuchi et al. (1993); Bogerd et al. (1993); Dasmahapatra et al. (1992); Germino et al. (1993); and Guarente (1993).

In the Examples which follow, the yeast host cell has two built-in reporters. The first reporter is the β-galactosidase enzyme. It is induced only after the tested protein-containing fusion product enters the cell nucleus, resulting in strong blue color of the yeast colonies. In addition, nuclear import of the fusion protein induces an auxotrophic marker HIS3, resulting in the ability of the yeast cells to grow on a histidine-deficient medium. Since histidine selection is known to be slightly leaky, the best results are achieved by including 3-amino-1,2,4,-triazole in the growth medium. The Examples which follow also utilize the yeast strain L40 as the host cell. This strain is the most suitable for the exemplified assay because it contains both reporter genes under inducible promoters activated by the LexA-GAL4AD fusion. This strain also is unable to grow in the absence of tryptophan and/or histidine, allowing for selective growth of cells containing the assay plasmid (TRP 1 marker) and/or induced reporter gene (HIS 3 marker). If the assay cassette, i.e. the fusion gene mLexA::GAL4AD(−)NLS, is transferred to another vector with a different auxotrophic growth marker (e.g., LEU or URA), the host strain has to be modified accordingly to allow the selective growth of the new plasmid.

The reporter gene(s) can be substituted with other reporters. For example, β-galactosidase can be exchanged with green fluorescent protein (GFP) and HIS3 replaced with URA3. Although GFP detection does not require specific staining used for the β-galactosidase assay, the latter may be more easily and accurately quantified. This quantification may be useful for comparisons of NLS activities between different proteins of interest or where the host cell has a first level of expression of the reporter gene.

The primary requirements in accordance with the subject invention are that a host cell be chosen which contains a reporter gene therein (located in the nucleus of the host cell), and that a DNA binding domain and an activation domain that interact with and activate that reporter gene, directly or indirectly, be chosen. Again, the DNA binding domain and the activation domain should be chosen such that neither of them contain a nuclear localization signal, which would lead to nuclear import of the fusion protein even if the protein of interest did not contain a nuclear localization signal (a false positive result). It should be readily apparent that a particular host cell could be recombinantly constructed to contain a desired reporter gene for use in the method of the invention.

The appropriate screening method for expression of the reporter gene depends upon the reporter gene chosen. For example, an assay for β-galactosidase is used to detect expression of the lacZ gene. Growth on a particular medium (i.e. a histidine deficient medium) can be used to detect expression of the HIS3 gene (referred to herein as a "selection marker" reporter gene). Such reporter genes and their appropriate screening methods are known in the art.

The methods and compositions of the subject invention require the construction of chimeric nucleic acid molecules and the introduction of such nucleic acid molecules into host cells. Routine techniques known in the art can be used to accomplish both of these tasks. In regard to the construction of chimeric nucleic acid molecules, the methods of Sambrook et al. (1989) are readily applicable.

In regard to introduction of such nucleic acid molecules into host cells, methods known in the art for introducing nucleic acid molecules into cells include lithium acetate transformation, and include microinjection (in which DNA is injected directly into the cytoplasm of cells through fine glass needles). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures. DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Viral vectors could also be used to introduce nucleic acid into host cells. Baculovirus is regularly used to introduce nucleic acid into insect cells. Viruses of mammalians cells, such as retrovirus, vaccinia virus, adenovirus, and adeno-associated virus (AAV), to name a few, can be used to introduce nucleic acid into mammalian host cells.

In addition to the method and other aspects of the invention described above, the subject invention provides a nucleic acid molecule encoding a modified LexA protein, wherein the modified LexA protein has no nuclear localization signal. The invention further provides a modified LexA protein, wherein the modified LexA protein has no nuclear localization signal. As indicated above, the nucleic acid molecule and the protein represent a modification of LexA which abolishes its intrinsic NLS activity but preserves its ability to bind promoter elements. Two specific amino acid changes in the LexA primary sequence were made, but, in principle, it is possible to alter other amino acids in LexA to achieve the same objectives, i.e. block the NLS function but retain the specific DNA binding to the LexA operators of the promoter. The modification of LexA uncouples nuclear import and promoter binding activities of LexA.

Figure 16:
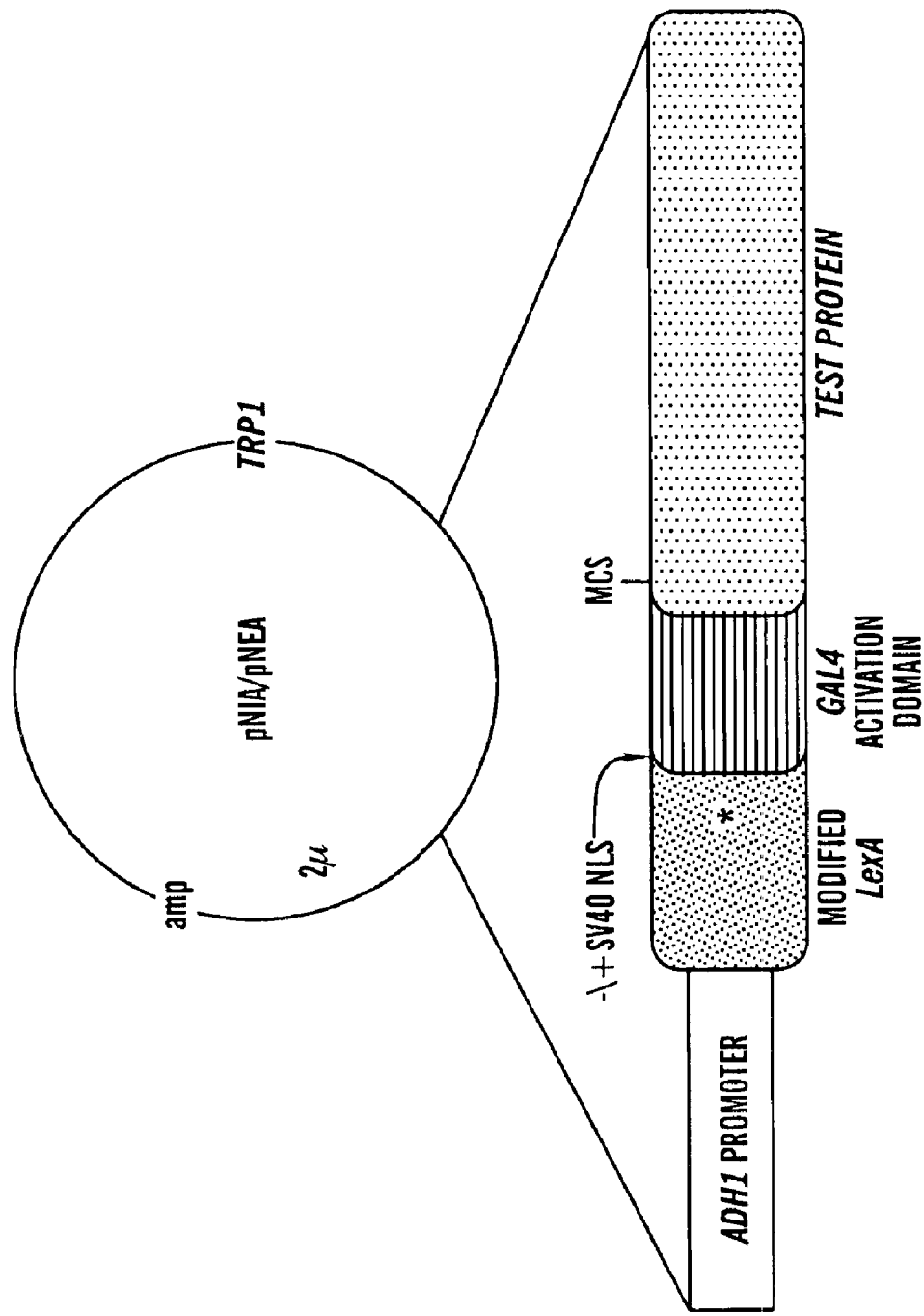
FIG. 16 is a schematic representation of pNIA and pNEA plasmids.

Much of the above discussion is equally applicable to the invention in regard to nuclear export. In this regard, the invention provides an expression vector comprising a chimeric nucleic acid molecule (which encodes a fusion protein, the fusion protein comprising a DNA binding domain for a reporter gene, an activation domain for the reporter gene, and a nuclear localization signal, wherein elements of the fusion protein have no nuclear export signal). In a presently preferred embodiment, the expression vector is a yeast one-hybrid expression vector, designated pNEA, which was designed to conveniently and rapidly assay the ability of proteins to exit the cell nucleus. pNEA expresses a fusion protein comprising a modified bacterial LexA (the DNA binding domain), yeast Gal4 activation domain, the SV40 large T-antigen NLS, and the tested protein encoded by a cDNA subcloned in-frame into the multiple cloning site downstream of Gal4 activation domain open reading frame (FIG. 16). When this expression vector is introduced into a host cell (having a nucleus having nucleic acid encoding the reporter gene therein), the fusion protein should enter the host cell nucleus due to the SV40 large T-antigen NLS. If the tested protein contains a functional nuclear export signal strong enough to override the NLS, the fusion protein will not enter the host cell nucleus and neither the LacZ gene nor the HIS3 gene will be activated.

As discussed above in regard to nuclear import, various host cells and elements of the expression vector can be selected for use in the assay for protein nuclear export. This includes variations in the promoter, DNA binding domain, activation domain, and reporter gene, as well as the NLS (replacing the SV40 large T-antigen NLS).

Likewise, the concept of direct and indirect affects on the expression of the reporter gene, and up- and down-regulation of the reporter gene, are equally applicable to the nuclear export aspect of the subject invention. If the tested protein includes a nuclear export signal, repression through a relay gene would then result in decreased export and therefore increased reporter gene expression (see above discussion in regard to nuclear import).

Materials and Methods

Yeast and Growth Conditions. Yeast cultures were grown and maintained in yeast extract/peptone/dextrose or the appropriate selective minimal medium using standard conditions (Kaiser et al. 1994). *Saccharomyces cerevisiae* strain L40 (MATa his3Δ200 trp1-901 leu2–3,112 ade2 lys2-801 am URA3::(lexAop)$_8$-lacZ LYS2::(lexAop)$_4$-HIS3) was used in all experiments (Hollenberg et al. 1995). For selective growth in the absence of histidine, the medium was supplemented, if necessary, with 3-amino-1,2,4-triazole (3AT) as specified for each specific experiment. Plasmids were introduced into yeast cells using the standard lithium acetate protocol (Kaiser et al. 1994).

DNA Constructions (see also Examples I and III). For pNIA and its fusion constructs, the Gal4 activation domain (Gal4AD), derived from the plasmid pGAD424, was PCR-amplified without the adjacent SV40 large T-antigen NLS. During amplification, EcoRI and BamHI restriction sites were introduced at the 5' and 3' ends of the amplified fragment, respectively. Then, a wild-type lexA gene in the vector pBTM116 (Hollenberg et al. 1995) was ligated in-frame with Gal4AD following restriction digestion of the corresponding purified PCR fragments with EcoRI and BamHI using standard molecular biology protocols (Ausubel et al. 1987). The resulting fusion construct was designated pLG. Next, the BamHI fragment of the VirE2 ORF from pET3b-VirE2 (Citovsky et al. 1988) was subcloned in-frame into the BamHI site of pLG, placing it immediately downstream of Gal4AD to produce pLGE2. Two amino acid residues of LexA within pLGE2 were mutated to produce the substitutions R157G and K159E by changing their codons CGC to GGC and AAA to GAA, respectively, using oligonucleotide directed mutagenesis with the Transformer™ Site-Directed Mutagenesis Kit (Clontech Laboratories, Inc.) according to the manufacturer's protocol. This procedure converted pLGE2 to pNIAE2. To produce pNIAD2, the VirE2 ORF in pNIAE2 was replaced with the BamHI fragment of VirD2 ORF from pGBTD2 (Ballas and Citovsky 1997).

For construction of pNEA, the same approach was employed except that the 5' primer for PCR amplification of Gal4AD included the sequence for the SV40 large T-antigen NLS, placing it at the amino terminus of Gal4AD. For pNEARev, the Rev ORF derived from pDM121 (Dr. D. McDonald, Salk Institute) was PCR-amplified, introducing BglII restriction sites at both ends of the fragment and ligated into the BamHI site of; pNEA. The M10 mutant of Rev was PCR-amplified from pM10 (Malim et al. 1989) introducing SmaI and PstI restriction sites at 5' and 3' ends of the amplified fragment, respectively, and subcloned into the SmaI and PstI sites of pNEA to produce pNEAM10. Similarly, RevΔ3 was PCR-amplified from pDM121Δ3NI (Dr. D. McDonald, Salk Institute) using the 5' and 3' primers containing SmaI and PstI recognition sequences, respectively, and subcloned into the SmaI and PstI sites of pNEA, resulting in the pNEARevΔ3 construct.

To obtain pNEACP, the BamHI and PstI sites were introduced at the 5' and 3' ends, respectively, of the tomato yellow leaf curl virus (TYLCV) CP ORF amplified by PCR from pTYH20 which contains the full length viral genome (Navot et al. 1991). The resulting fragment was ligated into the BamHI and PstI sites of pNEA. To generate pNEACPΔM, pNEACP was digested with StyI and ClaI, purified, treated with the Klenow fragment of the *E. coli* DNA polymerase, and self-ligated, preserving the correct reading frame. Finally, for pNEACPΔC, pNEACP was digested with PstI and ClaI, purified, sequentially treated with T4 DNA polymerase and the Klenow fragment of the *E. coli* DNA polymerase, and self-ligated.

Pfu polymerase (Stratagene) was used for all PCR reactions according to manufacturer's instructions. All mutations and ligation junctions were confirmed by DNA sequencing.

Analytical Methods. For quantitative determination of the β-galactosidase activity, the enzymatic assay was performed in liquid as described (Stachel et al. 1985). Qualitatively, β-galactosidase was assayed on nitrocellulose filters as described (Hollenberg et al. 1995).

For quantitation of growth, yeast cells were grown in tryptophan dropout minimal medium, harvested, and diluted to the optical density $A_{600}$=0.5. Serial 5-fold dilutions of the resulting cultures were prepared and 5 µl of each dilution was spotted onto selective medium plates lacking both tryptophan and histidine. As a control, the same amount of each dilution was spotted onto the minimal medium lacking only tryptophan.

EXAMPLE I
Construction of Vectors for the Genetic Assay of Nuclear Import

These constructs are designed to express fusion proteins composed of three functional parts: a modified LexA protein, an activation domain of the GAL4 protein, and a protein to be tested for its nuclear import. These components were obtained and joined together as follows:

(A) First, the Gal4 activation domain (AD), derived from the pGAD424 plasmid (FIG. 1), was PCR-amplified with and without the adjacent SV40 NLS (AD with NLS was used for positive control constructs, see below). During amplification, EcoRI and BamHI restriction sites were introduced at the 5' and 3' ends of the amplified fragment, respectively. The PCR mixtures contained the following components:

| (a) PCR of GAL4 AD without NLS | |
|---|---|
| Primer GAD5 (20 µM) | 5 µl |
| Primer GAD3BdE (20 µM) | 5 µl |
| dNTPs (10 mM each for dATP, dTTP, dGTP, dCTP) | 2 µl |
| Pfu reaction buffer (10X) | 10 µl |
| Template DNA (pGAD424, 10 ng/µl) | 5 µl |
| Pfu polymerase (0.5µ/µl) | 1 µl |
| Double distilled water | 72 µl |
| TOTAL | 100 µl |

Primer GAD5: SEQ ID NO:8:
5'-GGGAA TTCAA TTTTA ATCAA AGTGG G-3'
Primer GAD3BdE: SEQ ID NO:9:
5'-GACGG ATCCC CGGGT ATTCG ATCTC TT-3'

(b) PCR of GAL4 AD with NLS

| | |
|---|---|
| Primer GAD5NLS (20 µM) | 5 µl |
| Primer GAD3BdE (20 µM) | 5 µl |
| dNTPs (10 mM each for dATP, dTTP, dGTP, dCTP) | 2 µl |
| Pfu reaction buffer (10X) | 10 µl |
| Template DNA (pGAD424, 10 ng/µl) | 5 µl |
| Pfu polymerase (0.5 µ/µl) | 1 µl |
| Double distilled water | 72 µl |
| TOTAL | 100 µl |

Primer GAD5NLS: SEQ ID NO:10:
5'-GGGAA TTCGA TAAAG CGGAA TTAAT TCCC-3'
Primer GAD3BdE: SEQ ID NO:11:
5'-GACGG ATCCC CGGGT ATTCG ATCTC TT-3'

PCR conditions for all reactions:

| | |
|---|---|
| 94° C./2 min. | 1 cycle |
| 94° C./45 sec: 45° C./45 sec: 72° C./2 min. | 35 cycles |
| 72° C./10 min. | 1 cycle |

Figure 2:
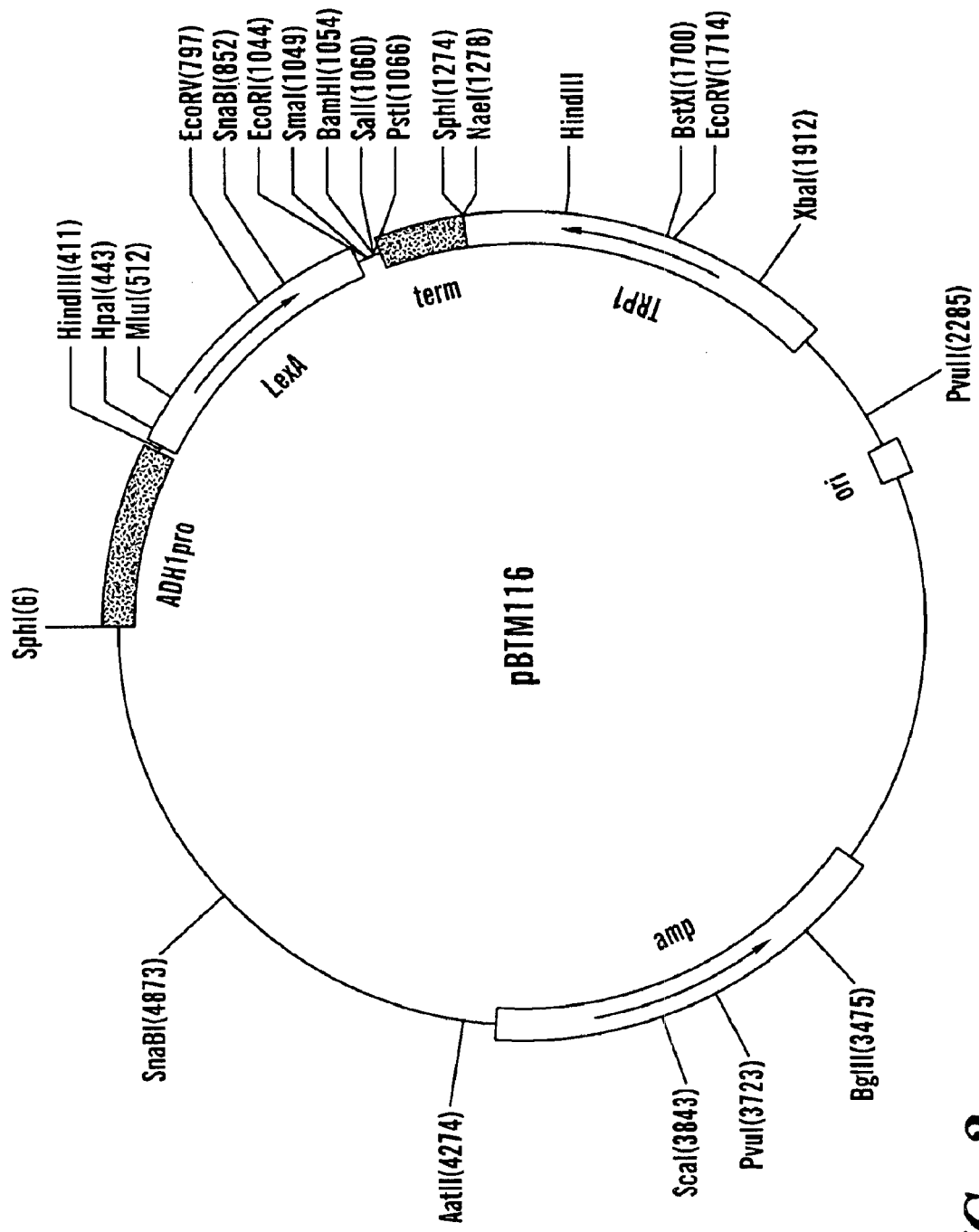
FIG. 2 is a map of pBTM116.

(B) Then, wild-type LexA in the pBTM 116 vector (FIG. 2) was joined in-frame with Gal4 AD following restriction digestion of the corresponding purified PCR fragments with EcoRI and BamHI using standard molecular biology protocols. The resulting fusion constructs were designated pLexA::GAL4AD (−)NLS and pLexA::GAL4AD (+)NLS.

(C) Next, two testing genes were introduced into pLexA::GAL4AD (−) NLS and pLexA::GAL4AD (+NLS vectors f or NLS-negative and NLS-positive controls.

Figure 3:
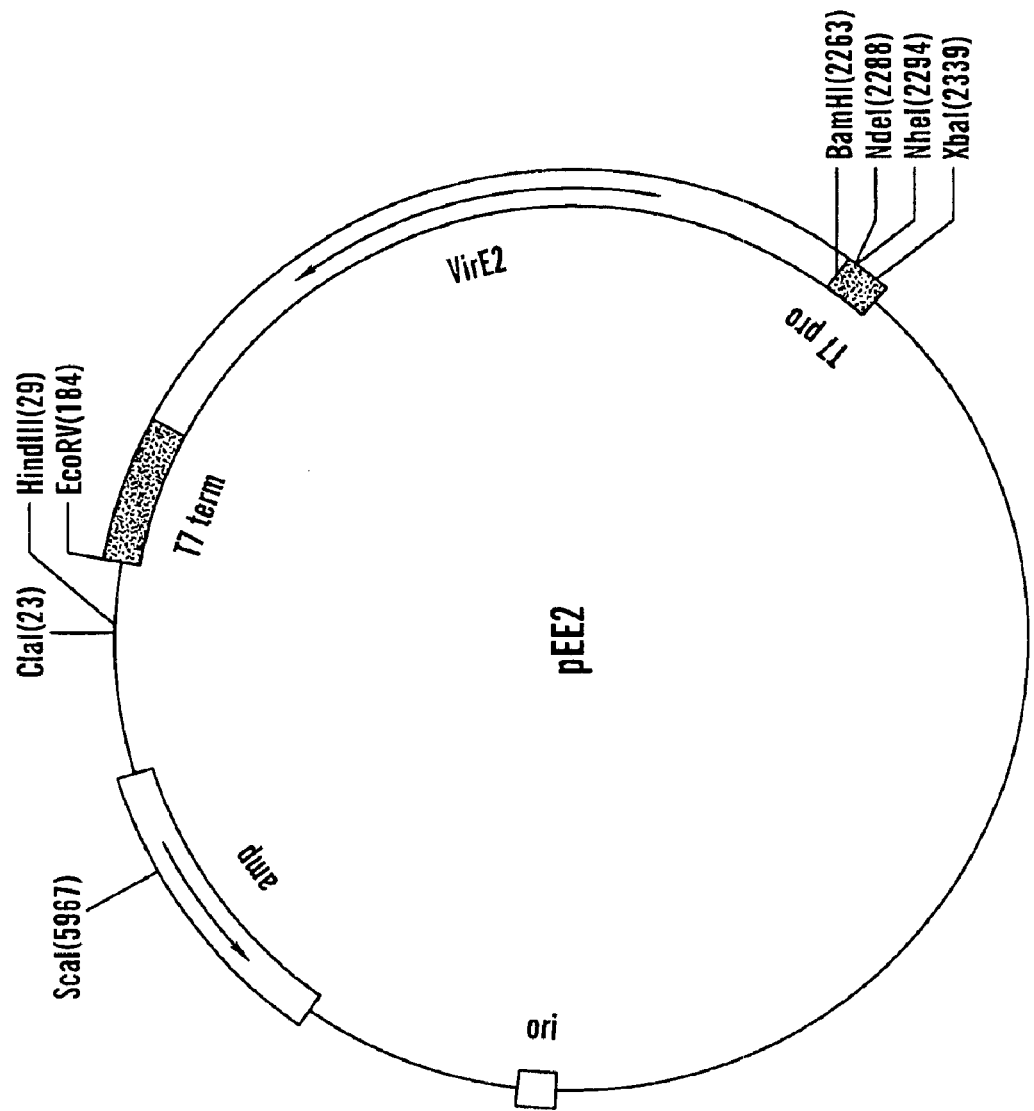
FIG. 3 is a map of pEE2.

(a) NLS-negative protein, VirE2 of *Agrobacterium tumefaciens*. VirE2 is known to remain cytoplasmic when expressed in yeast and animal cells, making it a suitable negative control for the nuclear import assay. The BamHI fragment of the pEE2 plasmid (FIG. 3) containing the VirE2 ORF was subcloned in-frame into the BamHI site of the pLexA::GAL4AD (−)NLS and pLexA::GAL4AD (+)NLS vectors, placing it immediately downstream of GAL4 AD.

Figure 4:
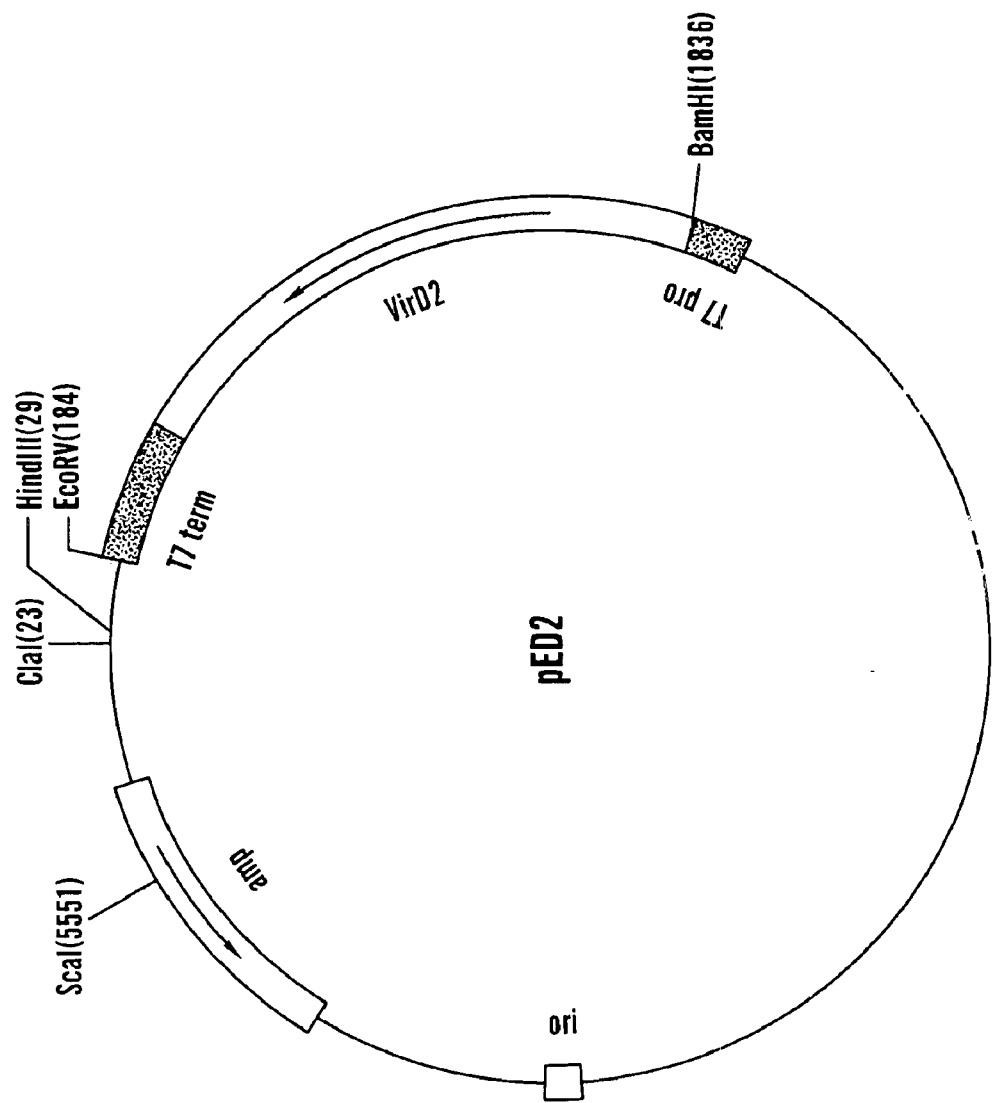
FIG. 4 is a map of pED2.

(b) NLS-positive protein, VirD2 of *Agrobacterium tumefaciens*. VirD2 is known to accumulate in the cell nucleus when expressed in yeast and animal cells, making it a suitable positive control for the nuclear import assay. The BamHI fragment of the pED2 plasmid (FIG. 4) containing the VirD2 ORF was subcloned in-frame into the BamHI site of pLexA::GAL4AD (−)NLS vector, placing it immediately downstream of Gal4 AD.

(D) Finally, the LexA gene in the above described constructs was modified to remove its part that encodes a functional nuclear localization sequence (NLS) which was identified by amino acid sequence analysis of LexA. This was performed by site directed mutagenesis using a TRANSFORMER™ Site-Directed Mutagenesis Kit (Cat.# K1600-1) from CLONTECH Laboratories, Inc. according to the manufacturer's protocol. Specifically, two amino acids in the LexA protein were mutated to produce substitutions R157G and K159E by changing their codons CGC to GGC and AAA to GAA, respectively (resulting in the nucleotide sequence shown in SEQ ID NO:2, encoding the amino acid sequence shown in SEQ ID NO:1). The sequences for the mutagenesis primers were:

Mutant primer [designated LexA(−NLS)]: SEQ ID NO:12:
5'-CCGTT AAGGG CCTGG AAAAA CAGGG-3'

Selection primer (designated ScaI-to-StuI): SEQ ID NO:13:
5'-GTGAC TGGTG AGGCC TCAAC CAAGT C-3'

Figure 5:
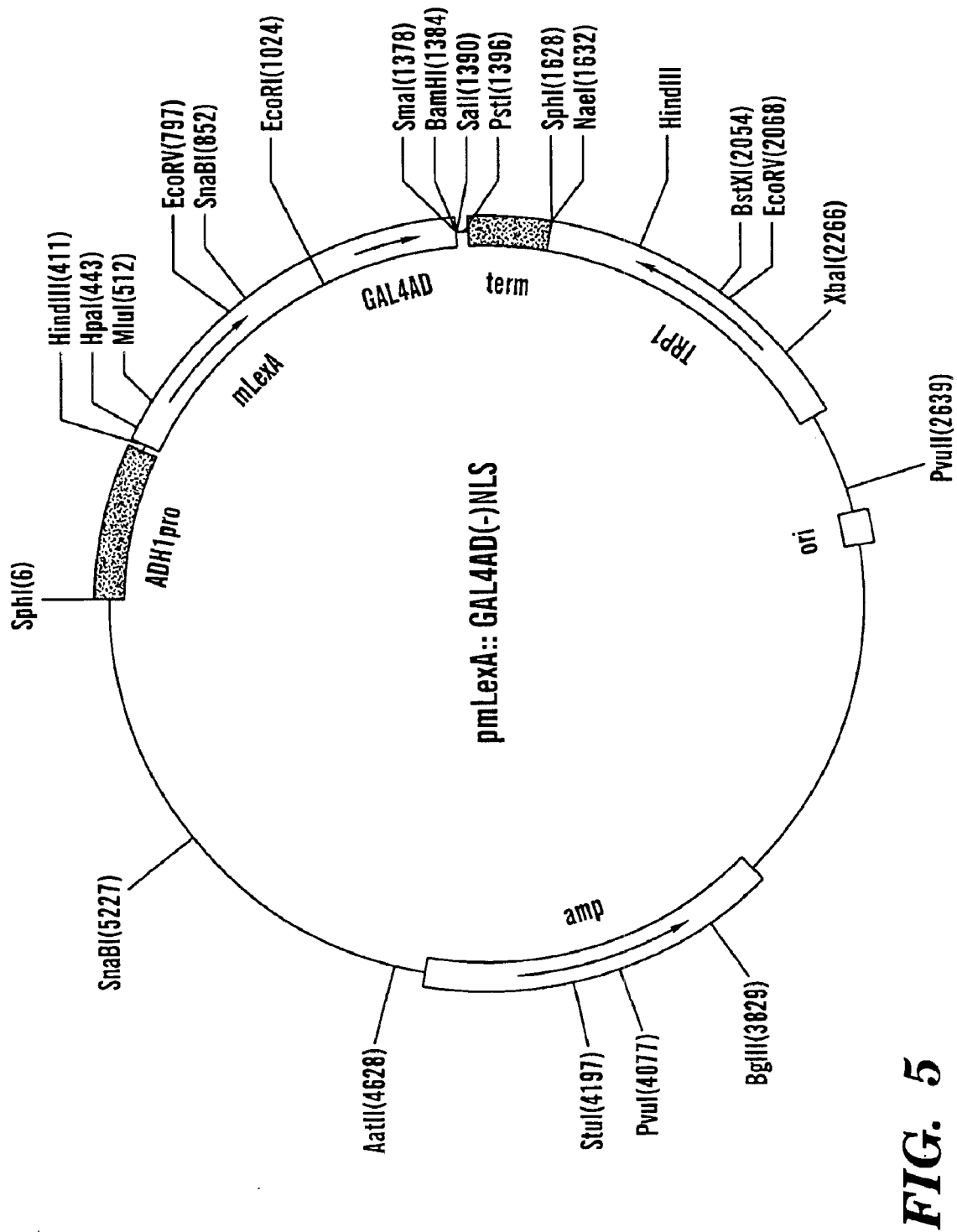
FIG. 5 is a map of pmLexA::GAL4AD(-)NLS.
Figure 6:
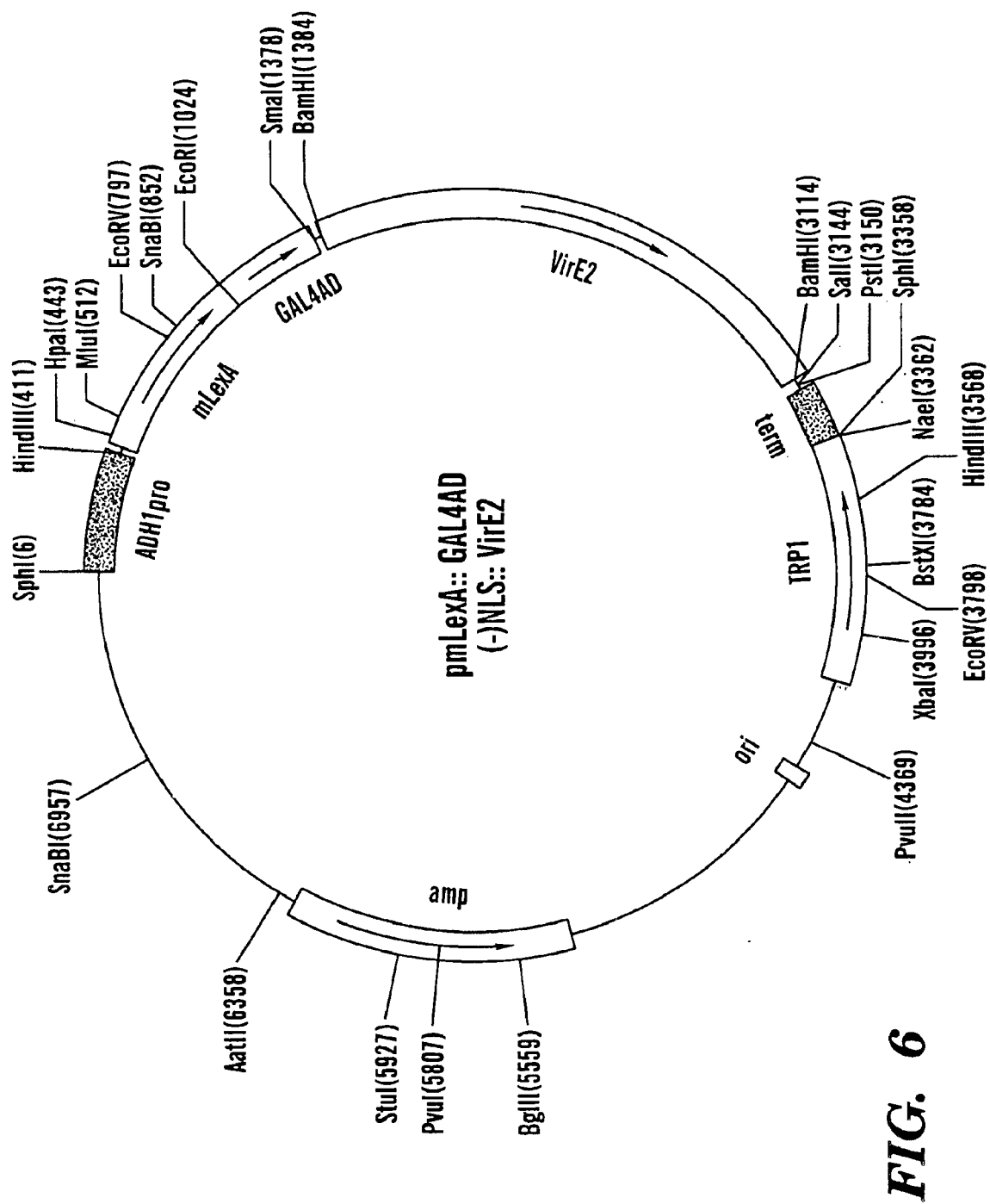
FIG. 6 is a map of pmLeXA::GAL4AD(-)NLS::VirE2.
Figure 7:
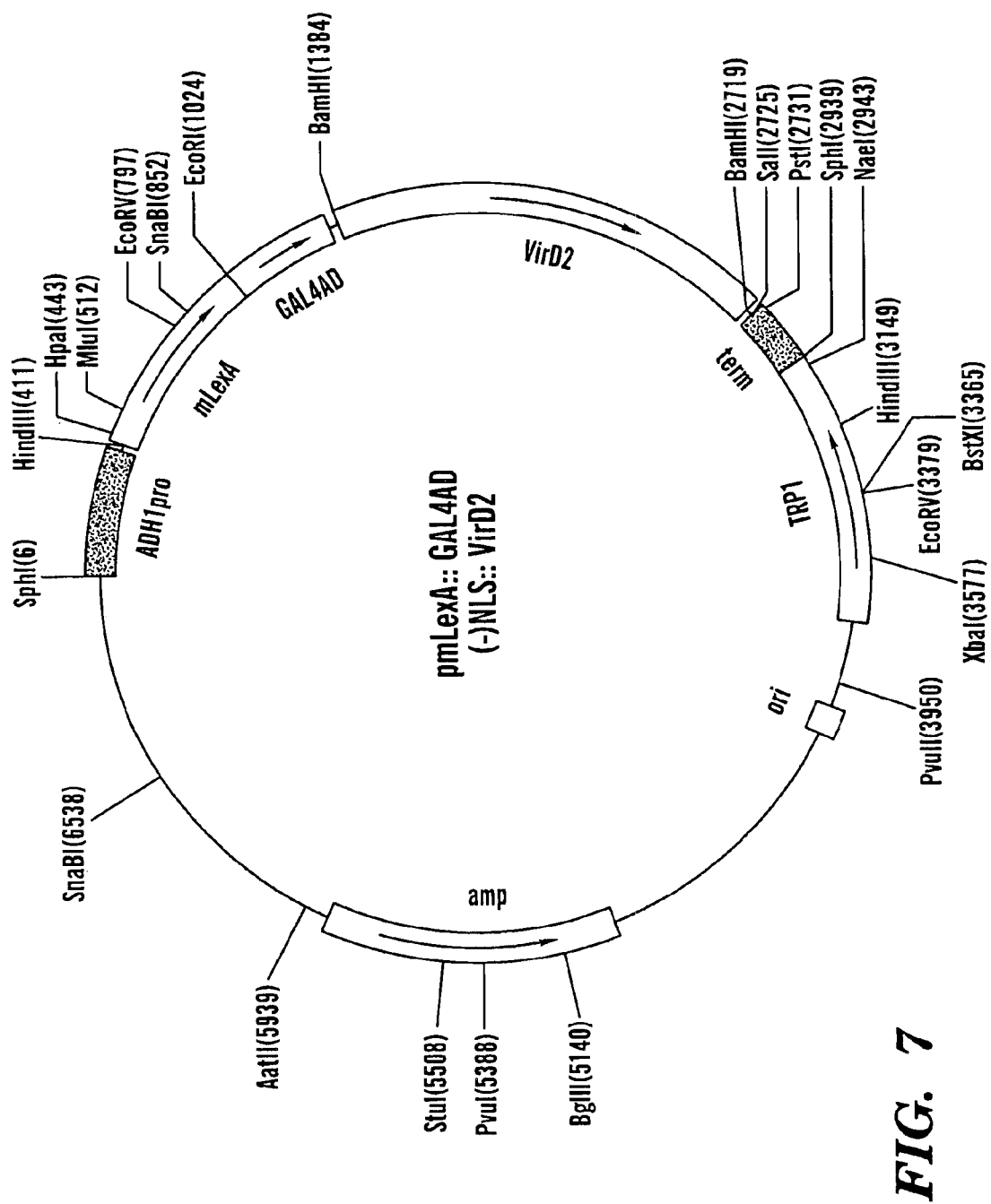
FIG. 7 is a map of pmLeXA::GAL4AD(-)NLS::VirD2.
Figure 8:
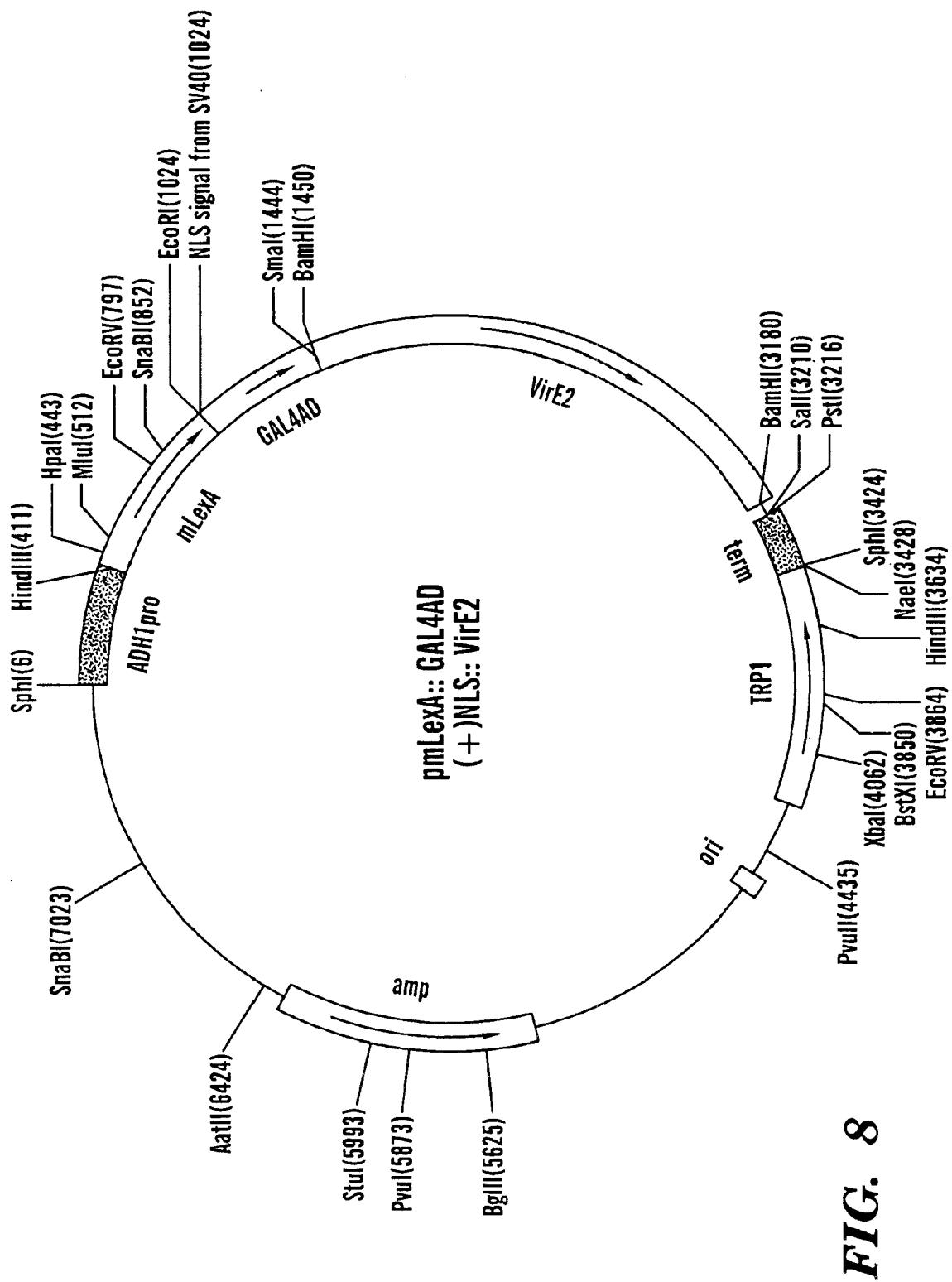
FIG. 8 is a map of pmLexA::GAL4AD(+)NLS::VirE2.
Figure 9:
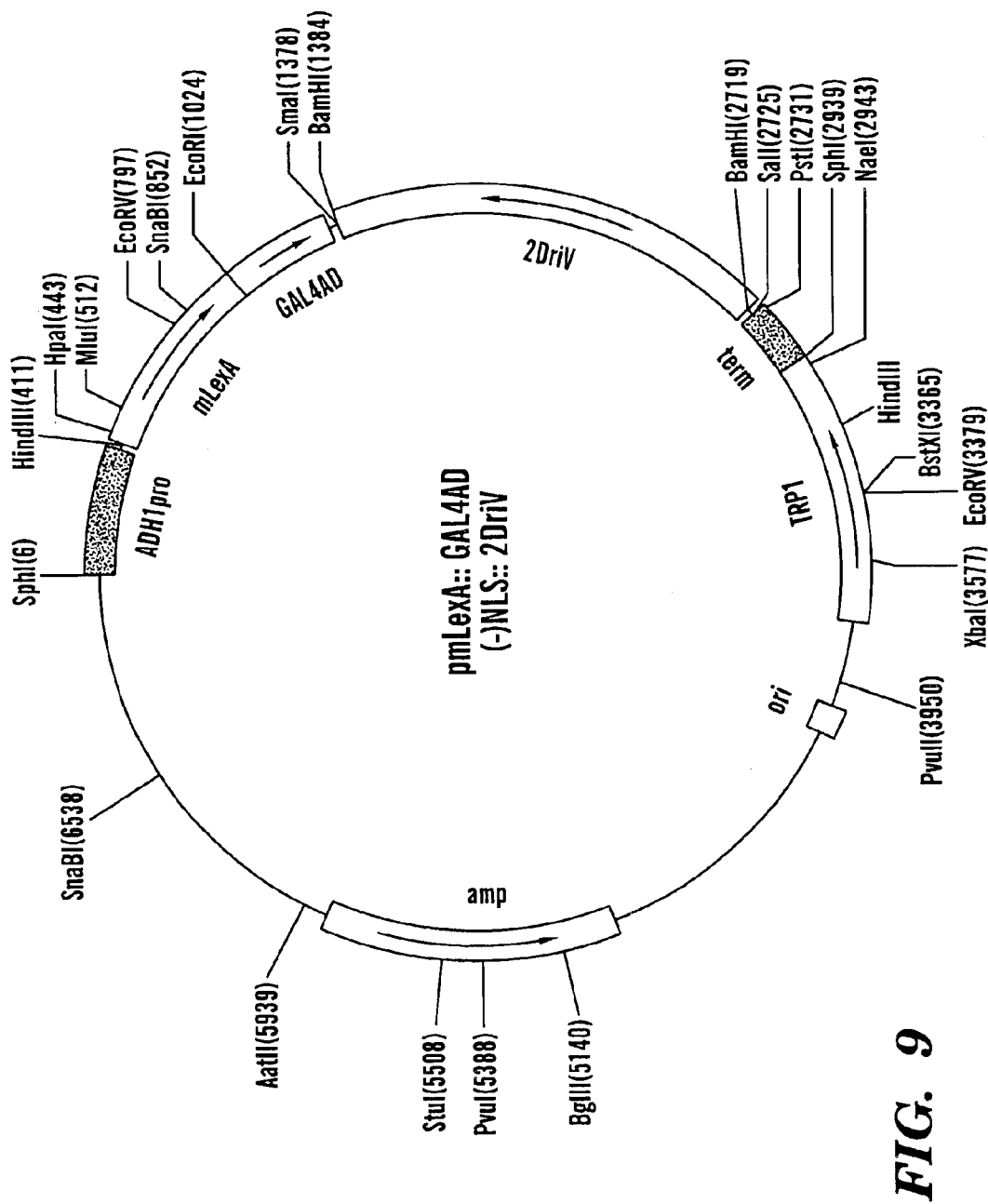
FIG. 9 is a map of pmLeXA::GAL4AD(-)NLS::2DriV.

This procedure produced a modified LexA which was designated mLexA. Collectively, the above described procedures yielded the following five constructs:

1. pmLexA::GAL4AD (−)NLS (FIG. 5) assay vector, the experimental construct in which the gene of interest should be subcloned in-frame
2. pmLexA::GAL4AD (−)NLS::VirE2 (FIG. 6) negative import control for the assay
3. pmLexA::GAL4AD (−)NLS::VirD2 (FIG. 7) positive import control for the assay
4. pmLexA::GAL4AD (+)NLS::VirE2 (FIG. 8) positive control for the ability of the experimental construct to produce fusion protein capable of nuclear import, i.e. that the protein of interest does not non-specifically alter the conformation of the fusion protein, preventing nuclear import even in the presence of an active NLS
5. pmLexA::GAL4AD (−)NLS::2DriV (FIG. 9) another negative control containing antisense orientation of VirD2

All these plasmids are $Amp^r$ and TRP1, requiring growth on an ampicillin-containing medium in *E. coli* and on a tryptophan drop-out medium in yeast cells.

EXAMPLE II
One-Hybrid Genetic Assay for Protein Nuclear Import

The fusion protein derived from pLexA::GAL4AD (−)NLS::VirE2 enters the cell nucleus and activates the reporter gene expression, indicating that LexA carries a cryptic NLS although it is a prokaryotic protein and is not expected to enter the nucleus. Thus it was necessary to identify and disable this signal, resulting in a modification of the LexA protein (see item D above).

The fusion protein derived from pmLexA:: GAL4AD (–)NLS, which lacks a tested protein, enters the cell nucleus by diffusion due to its small size (approximately 38 kDa). This import, however, is less efficient than that of NLS-containing fusion products, resulting in a weaker expression of the β-galactosidase reporter. Nevertheless, it is recommended to use pmLexA::GAL4AD (–)NLS::VirE2 as a negative control for the assay. This 106 kDa fusion protein does not enter the nucleus at all, producing zero expression of the reporter.

The user has an option of constructing his/her own custom made negative control for this assay by subcloning the protein of interest in antisense orientation. Results indicate that VirD2, which targets the fusion product derived from pmLexA::GAL4AD (–)NLS::VirD2 to the nucleus, does not promote nuclear import when subcloned into the same vector in antisense orientation, i.e. pmLexA::GAL4AD (–)NLS::2DriV.

The current version of pmLexA::GAL4AD (–)NLS includes only four unique cloning sites, SmaI, BamHI, SalI and PstI, for insertion of the gene of interest. However, additional sites can be easily engineered, if required, using simple standard cloning techniques.

Once the gene of interest is inserted in-frame into the pmLexA::GAL4AD (–)NLS assay vector, it can be transformed into the L40 yeast strain (MAT α his3Δ200 trp1-90 leu2-3,112 ade2, lys2::LYS2::LexAHIS3, ura3::URA3::LexA lacZ gal80) by any standard procedure using either Lithium acetate or electroporation (Ausubel et al. 1987). For negative and positive controls, the appropriate constructs (described above) are separately introduced into L40 cells.

The resulting yeast strains are grown on a selective medium and assayed for β-galactosidase activity after one or two days of growth using standard procedures. A positive result, i.e. dark blue-stained yeast colonies, indicates active nuclear import of the fusion protein and, consequently, the presence of a functional NLS in the tested protein.

EXAMPLE III

Nuclear import assay. The basic strategy of these experiments is based on expression in yeast cells of a triple-fusion protein comprising bacterial LexA, yeast Gal4 activation domain (Gal4AD), and the tested protein encoded by a cDNA subcloned in-frame downstream of Gal4AD (FIG. 16). If the tested protein contains a functional NLS, the fusion product will enter the yeast cell nucleus. Following this nuclear import, the LexA domain will target the fusion protein to the LexA operator sites of the reporter lacZ gene contained in the L40 yeast strain. Gal4AD then activates the expression of lacZ, resulting in β-galactosidase activity. In the absence of a NLS, the fusion protein is unable to reach the cell nucleus and, thus, activate the reporter gene.

In addition to induction of the β-galactosidase reporter, this one-hybrid system allows direct selection for the nuclear import of the tested protein in the same L40 yeast strain, which contains an integrated copy of the HIS3 gene with upstream LexA operators. Only cells expressing the NLS-containing fusion protein will grow on a histidine-deficient medium.

Clearly, the success of this approach hinges on the inability of LexA-Gal4AD-tested protein fusions to enter the cell nucleus in the absence of an NLS contained within the tested protein. Thus, neither LexA nor Gal4AD should contain NLS sequences. While Gal4AD is known to lack NLS (Silver et al. 1988), LexA, a bacterial protein, is generally thought not to have evolved such a signal. Surprisingly, however, the studies herein demonstrated that a LexA-Gal4AD fusion containing VirE2, an *Agrobacterium* protein shown to lack an NLS functional in animal cells (Guralnick et al. 1996), induced the β-galactosidase reporter (FIG. 18, pLGE2 construct) and grew on a histidine dropout medium (FIG. 19, pLGE2 construct).

VirE2 is a large protein (70 kDa); thus, the LexA-Gal4AD-VirE2 fusion is likely to be actively imported into the cell nucleus to allow this gene induction. Because the absence of NLS in LexA was implied from its bacterial origin rather than demonstrated directly, it is possible that LexA carries a previously unidentified NLS signal. Inspection of the amino acid sequence of LexA identified a short stretch of basic residues (FIG. 17) which may function as an NLS. Two amino acid substitutions, R157G and K159E, were made in this motif (FIG. 17), resulting in a modified LexA (mLexA) within the triple-fusion expression vector, designated pNIA (Nuclear Import Assay). FIGS. 18 and 19 show that mLexA expressed in fusion with Gal4AD and VirE2 from the pNIAE2 construction no longer activated the reporter genes lacZ (FIG. 18) and HIS3 (FIG. 19), indicating the lack of nuclear import of the fusion protein.

To exclude a possibility that LexA mutagenesis non-specifically inactivated this protein, a short amino acid sequence corresponding to the SV40 large T-antigen NLS was introduced between the mLexA and Gal4AD domains of pNIAE2, producing pNIA(+)E2. The fusion protein produced from this construct localized to the cell nucleus, resulting in lacZ induction (FIG. 18) and cell growth in the absence of histidine (FIG. 19) and indicating mLexA functionality in activation of gene expression. Note that the presence of the tested protein within the pNIA construction is essential for detection of bona fide nuclear import; in the absence of the tested protein, the mLexA-Gal4AD fusion produced from pNIA alone may simply diffuse into the nucleus due to its small size (data not shown).

Next, pNIA was used to test its ability to detect a functional NLS within a known nuclear protein. To this end, an NLS-containing protein, VirD2 of *Agrobacterium* (Citovsky et al. 1994; Howard et al. 1992), was subcloned into pNIA (pNIAD2 construction). The resulting mLexA-Gal4AD-VirD2 fusion protein was imported into the cell nucleus as illustrated by activation of the reporter genes lacZ (FIG. 18) and HIS3 (FIG. 19). When, as a negative control, a VirD2 cDNA sequence was inserted into pNIA in the antisense orientation, the fusion product did not activate the reporter genes (data not shown). These results demonstrate the pNIA allows detection of and selection for proteins containing a functional NLS sequence.

More particularly, FIG. 16 shows the plasmid compositions. pNIA expresses a fusion protein consisting of mLexA, Gal4AD, and protein-to be tested; pNEA produces a fusion between mLexA, SV40 NLS, Gal4AD, and a tested protein. Asterisk indicates the position of the LexA NLS. MCS indicates the multiple cloning sites that include the sites for SmaI, BamHI, SalI, and PstI restriction endonucleases. The plasmid backbone is derived from pBTM116 (Hollenberg et al. 1995). FIG. 17 shows the LexA NLS and amino acids substitutions (asterisks) which inactivate this signal, producing modified LexA (mLexA). Numbers indicate the position of the nucleotides (top) and amino acid residues (bottom) within LexA gene and protein sequences, respectively.

FIGS. 18 and 19 show the results of the nuclear import assay. FIG. 18 shows the β-galactosidase assay following cell growth on minimal medium without tryptophan. FIG. 19 shows the selection assay by cell growth on minimal medium deficient for both tryptophan and histidine and supplemented with 5 mM of 3AT. pLGE expresses VirE2 fused to wild-type LexA and Gal4AD, pNIAE2 expresses VirE2 fused to modified LexA (mLexA) and Gal4AD, pNIAE2 expresses VirE2 fused to mLexA, SV40 NLS, and Gal4AD, and pNIAD2 expresses VirD2 fused to mLexA and Gal4AD.

EXAMPLE IV

Construction of Vectors for the Genetic Assay of Nuclear Export

These constructs are designed to express fusion proteins composed of three functional parts: a modified LexA protein, activation domain of the GAL4 protein, and a protein to be tested for its nuclear export. These components were obtained and joined together as follows:

(A) First, the Gal4 activation domain (AD) with the adjacent SV40 NLS, derived from the pGAD424: plasmid (FIG. 1), was PCR-amplified. During amplification, EcoRI and BamHI restriction sites were introduced at the 5' and 3' ends of the amplified fragment, respectively. The PCR mixtures contained the following components:

| | |
|---|---|
| Primer GAD5NLS (20 μM) | 5 μl |
| Primer GAD3BdE (20 μM) | 5 μl |
| dNTPs (10 mM each for dATP, dTTP, dGTP, dCTP) | 2 μl |
| Pfu reaction buffer (10X) | 10 μl |
| Template DNA (pGAD424, 10 ng/μl) | 5 μl |
| Pfu polymerase (0.5μ/μl) | 1 μl |
| Double distilled water | 72 μl |
| TOTAL | 100 μl |

Primer GAD5NLS: SEQ ID NO:10:
5'-GGGAA TTCGA TAAAG CGGAA TTAAT TCCC-3'
Primer GAD3BdE: SEQ ID NO:11:
5'-GACGG ATCCC CGGGT ATTCG ATCTC TT-3'
PCR conditions for all reactions:

| | |
|---|---|
| 94° C./2 min. | 1 cycle |
| 94° C./45 sec: 45° C./45 sec: 72° C./2 min. | 35 cycles |
| 72° C./10 min. | 1 cycle |

(B) Then, wild-type LexA in the pBTM116 vector (FIG. 2) was joined in-frame with Gal4 AD following restriction digestion of the corresponding purified PCR fragments with EcoRI and BamHI using standard molecular biology protocols. The resulting fusion construct was designated pLexA::GAL4AD (+)NLS.

(C) Next, the LexA gene in pLexA::GAL4AD (+)NLS was modified to remove its part that encodes a functional nuclear localization sequence (NLS) which had been identified by amino acid sequence analysis of LexA. This as performed by site directed mutagenesis using Transformer™ Site-Directed Mutagenesis Kit (Cat.# 1600-1) from CLONTECH Laboratories, Inc. according to the manufacturer's protocol. Specifically, two amino acids in the LexA protein were mutated to produce substitutions R157G and K159E by changing their codons CGC to GGC and AAA to GAA, respectively. The sequences or the mutagenesis primers were:

Mutant primer [designated LexA(-NLS)]: SEQ ID NO:12:
5'-CCGTT AAGGG CCTGG AAAAA CAGGG-3'

Selection primer (designated ScaI-to-StuI): SEQ ID NO:13:
5'-GTGAC TGGTG AGGCC TCAAC CAAGT C-3'

Figure 13:
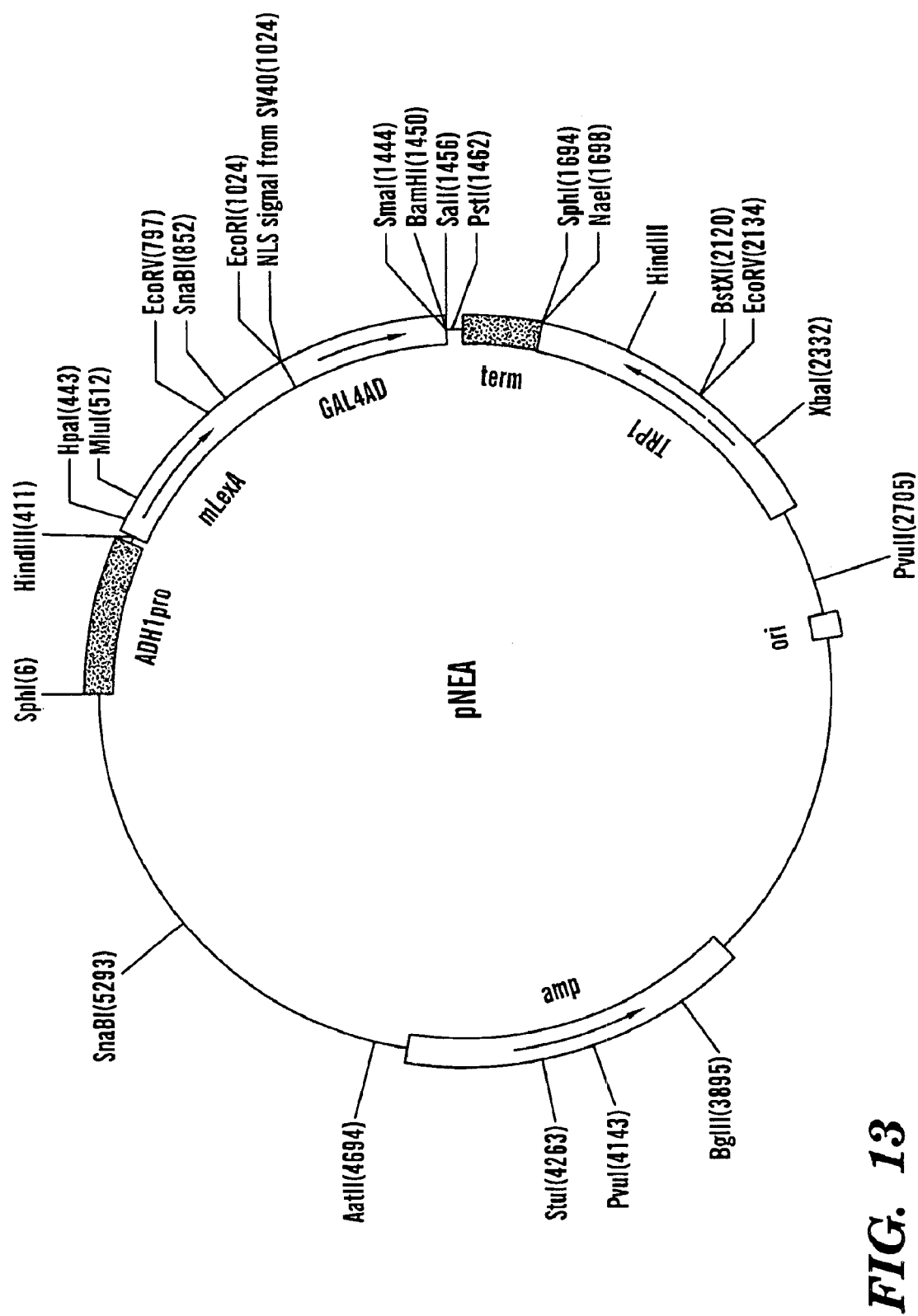
FIG. 13 is a map of pNEA.

This procedure produced a modified LexA which was designated mLexA, resulting in the pmLexA::GAL4AD (+)NLS construct, also designated pNEA (FIG. 13)(nuclear export assay).

(D) Finally, two testing genes were introduced into pNEA for NES-negative and NES-positive controls.

(a) NES-negative protein, VirE2 of *Agrobacterium tumefaciens*. VirE2, known to lack NES, was used as negative control for the nuclear export assay. BamHI fragment of pEE2 plasmid (FIG. 3) containing the VirE2 ORF was subcloned in-frame into the BamHI site of pNEA, placing it immediately downstream of GAL4 AD.

(b) NES-positive protein, Rev of HIV type-1 virus. Rev is a known nuclear shuttle protein which contains a leucine-rich NES, making it a suitable positive control for the nuclear export assay. Rev cDNA was PCR-amplified as a BglII fragment from pDM121 (McDonald et al. (1998)) and subcloned in-frame into the BamHI site of pNEA, placing it immediately downstream of Gal4 AD.

Figure 14:
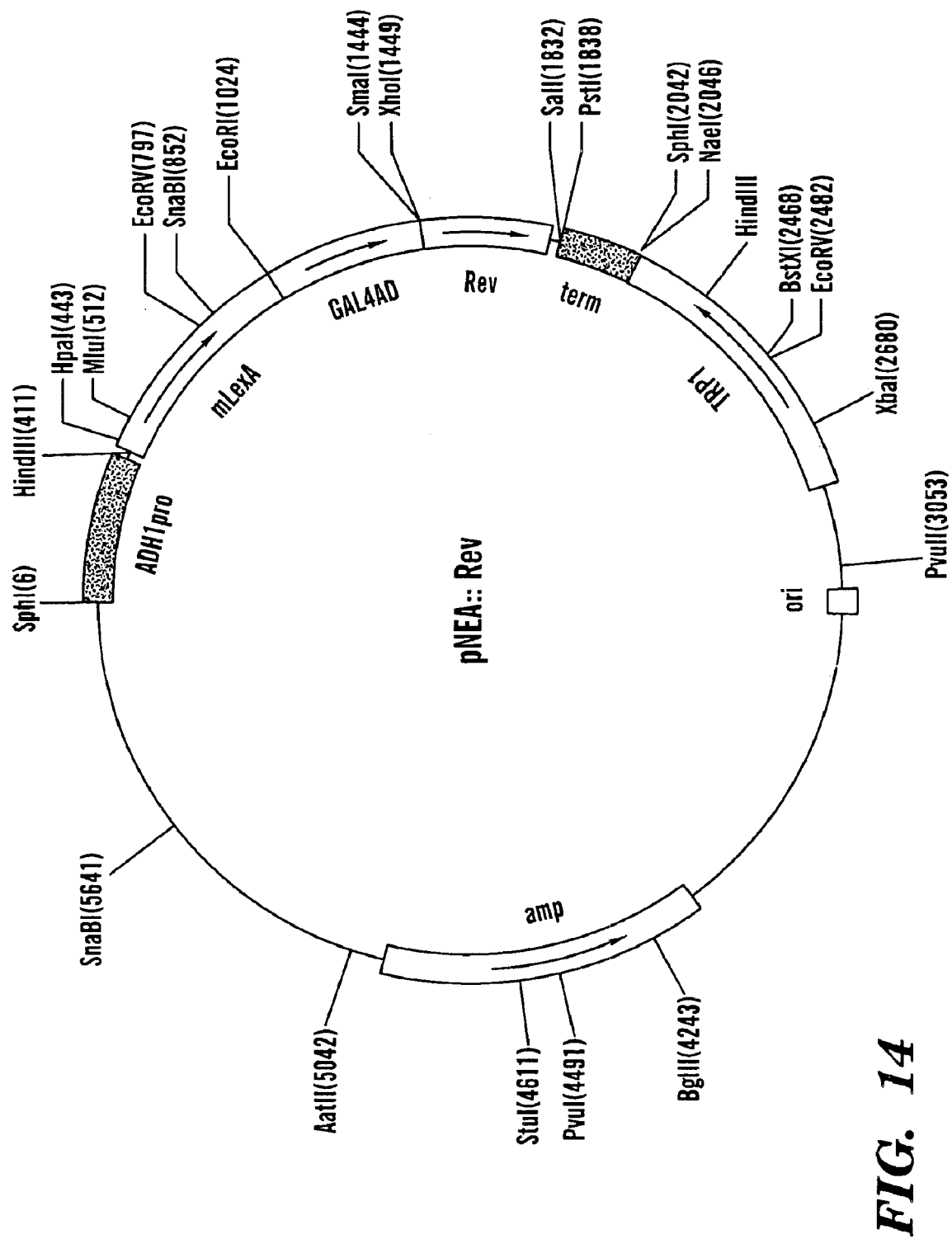
FIG. 14 is a map of pNEA::Rev.
Figure 15:
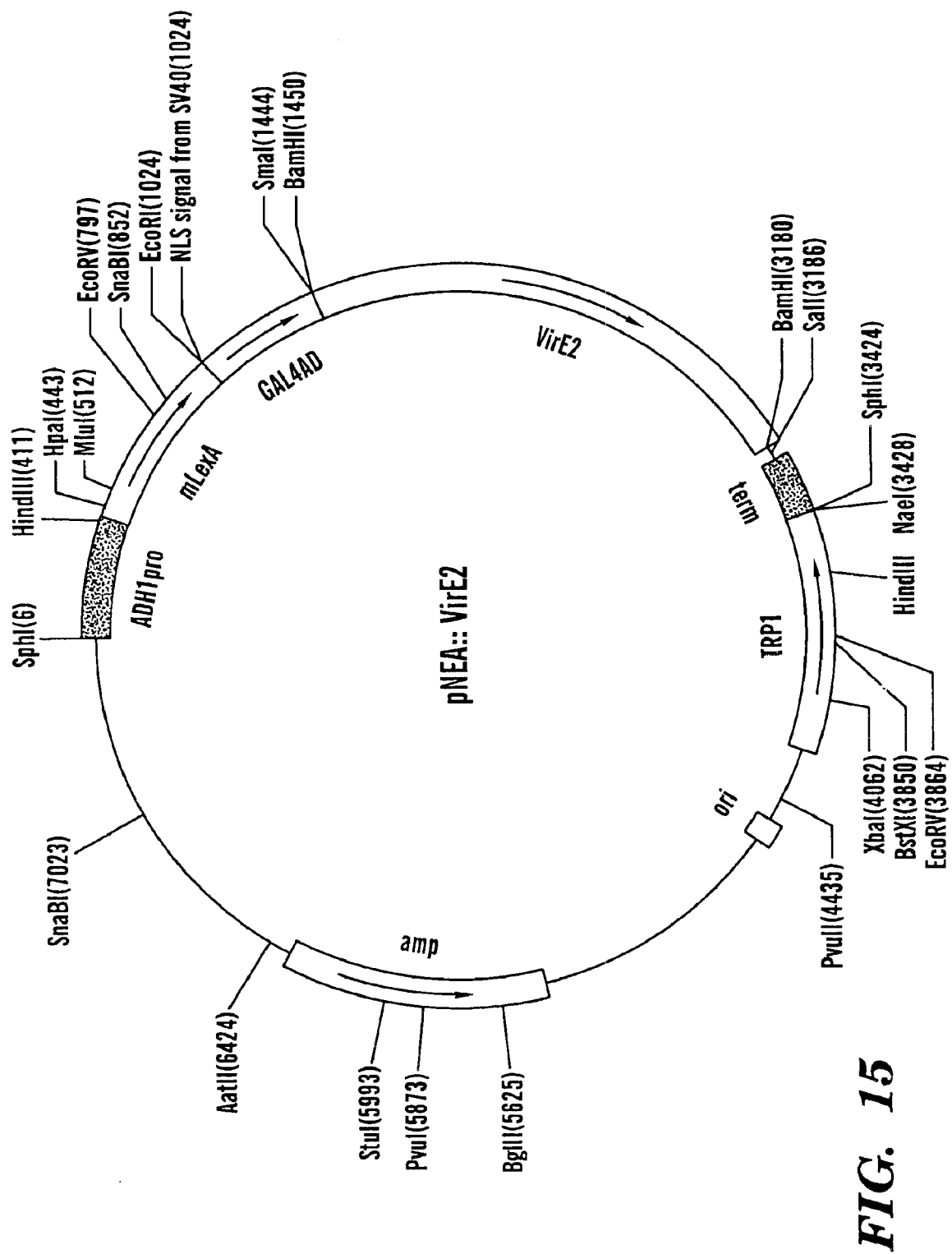
FIG. 15 is a map of pNEA::VirE2.

Collectively, the described above procedures yielded the following three constructs:
1. pNEA (FIG. 13)
   assay vector, the experimental construct in which the gene of interest should be subcloned in-frame
2. pNEA::VirE2 (FIG. 15)
   negative import control for the assay
3. pNEA::Rev (FIG. 14)
   positive import control for the assay All these plasmids are Amp$^r$ and TRP1, requiring growth on an ampicillin-containing medium in *E. coli* and on a tryptophan drop-out medium in yeast cells.

EXAMPLE V

One-Hybrid Genetic Assay for Protein Nuclear Export

Once the gene of interest is inserted in-frame into the pNEA assay vector, it can be transformed into the L40 yeast strain (MATa his3Δ200 trp1-90 leu2-3,112 ade2, lys2::LYS2::lexAHIS3, ura3::URA3::lexA lacZ gal80) by any standard procedure using either lithium acetate or electroporation (Ausubel et al. 1987). For negative and positive controls, the appropriate constructs (described above) are separately introduced into L40 cells.

The resulting yeast strains are grown on a selective medium and assayed for β-galactosidase activity after one or two days of growth using standard procedures. The appearance of white yeast colonies indicates active nuclear export of the fusion protein and, consequently, the presence of a functional NES in the tested protein.

In addition, nuclear import of the fusion product in L40 induces an auxotrophic marker HIS3, resulting in the ability of the yeast cells to grow on a histidine-deficient medium. Thus, if cells transformed with pNEA carrying the gene of interest are plated first on tryptophan-deficient medium to select for the pNEA construct and then replica-plated on a tryptophan-histidine double dropout medium, nuclear export will be indicated by the appearance of yeast colonies that grow in the absence of tryptophan but do not grow in the absence of histidine.

EXAMPLE VI

Nuclear export assay. The ability of pNIA to detect protein transport into the nucleus can also be utilized to assay for a reverse protein traffic, i.e., nuclear export. To this end, the SV40 large T-antigen NLS was introduced between mLexA and Gal4AD of pNIA, resulting in a Nuclear Export Assay plasmid pNEA (FIG. 16). The separate SV40 NLS rather than the internal NLS of wild-type LexA was chosen to retain the modular composition of the vector and utilize the same mLexA component as in the nuclear import assay, facilitating direct comparison of results obtained with the pNIA and pNEA constructs. In pNEA, fusion to a protein without an NES will result in nuclear import due to the presence of the SV40 NLS. Yeast cells harboring this construction will express β-galactosidase and grow in the absence of histidine. Indeed, as mentioned above, subcloning of VirE2 into pNEA (same as pNIA(+)E2 construction) resulted in a strong β-galactosidase staining (FIG. 18) and histidine prototrophy (FIG. 19). Note that VirE2 in pNIA did not induce these effects (FIGS. 18 and 19).

Fusion to an NES-containing protein, on the other hand, is expected to redirect the protein product into the cell cytoplasm, at least partly abolishing the β-galactosidase activity and impeding growth without histidine. This idea was tested using the Rev protein of HIV-1 known to carry a functional NES (Ullman et al. 1997). Expression of Rev from the pNEA vector dramatically decreased β-galactosidase activity to about 12% of that observed with pNEA alone (FIG. 20), suggesting the predominantly cytoplasmic localization of the fusion product. Residual levels of lacZ activity are probably due to a small steady-state pool of Rev protein within the cell nucleus due to its nuclear shuttling activity (Pollard et al. 1998).

Figure 20:
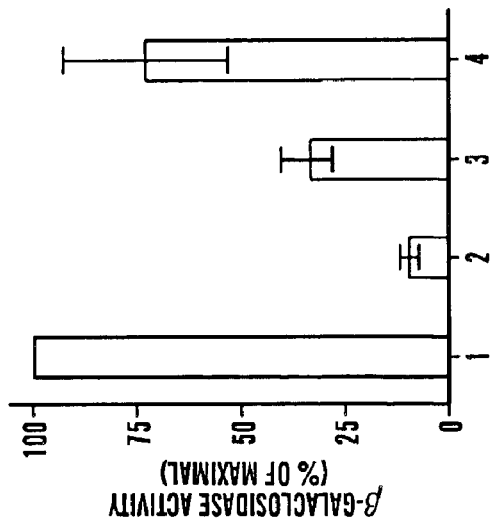
FIG. 20 illustrates the results of a β-galactosidase assay used to detect nuclear export of a tested protein.

That the decrease in lacZ induction specifically depends on the Rev NES was demonstrated by mutating or deleting this signal. First, the M10 mutant of Rev (Malim et al. 1989) was introduced into pNEA. FIG. 20 shows that the M10 NES mutation, which substitutes only two amino acid residues within NES (Malim et al. 1989), restored the β-galactosidase activity to 30% that of the maximum, indicating diminished nuclear export of the mutant fusion protein as compared to the wild-type Rev. A deletion mutation of the Rev NES, RevΔ3, which removes most of the signal sequence (Taagepera et al. 1998), increased lacZ reporter gene induction to 70% to 90% of the maximal level (FIG. 20).

Figure 22:
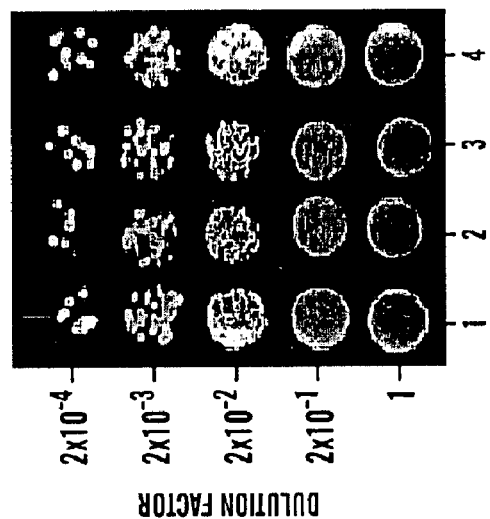
FIG. 22 illustrates the results of the selective reporter gene (HIS3) used to detect nuclear export of a tested protein (medium deficient for only tryptophan)
Figure 21:
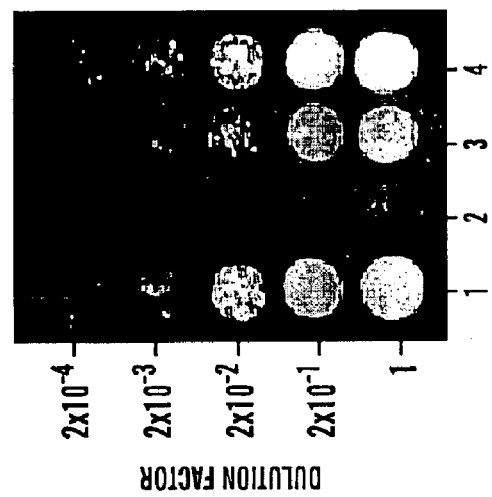
FIG. 21 illustrates the results of the selective reporter gene (HIS3) used to detect nuclear export of a tested protein (medium deficient for both tryptophan and histidine)

Changes in the degree of lacZ gene expression caused by the Rev NES closely paralleled HIS3 expression. Serial dilutions of yeast cell cultures plated on the histidine dropout selective medium clearly demonstrated a dramatic reduction in histidine prototrophy supported by the Rev fusion product. This effect was NES-dependent because both the M10 and RevΔ3 mutations gradually restored growth on the selective medium.(FIG. 21). In the absence of selection, all strains exhibited equal growth (FIG. 22). These results indicate that the degree of repression of the lacZ and HIS3 reporter genes and, by implication nuclear export, directly reflects the strength of the NES signal, allowing the use of this nuclear export assay to give a quantitative indication of and select for the activity of NES signals in proteins of interest.

More particularly, FIGS. 20–22 shows the results of the nuclear export assay. FIG. 20 shows the quantitative β-galactosidase assay in liquid following cell growth in minimal medium without tryptophan. Standard errors are shown based on five independent experiments. β-galactosidase activity is expressed as percent of maximal enzymatic activity (usually 100–200 units) obtained with pNEA alone. FIG. 21 shows the selection assay by cell growth on minimal medium deficient for both tryptophan and histidine and supplemented with 100 mM 3AT. This 3AT concentration was optimal for detecting differences in cell growth between various Rev derivatives. FIG. 22 shows cell growth on minimal medium deficient for only tryptophan. (1), pNEA alone; (2), pNEARev (NES: SEQ ID NO:5: LPPLERLTL); (3), pNEAM10 (mutated NES: SEQ ID NO:6: LPPDLRLTL); (4), pNEARevΔ3 (residual NES: SEQ ID NO:7: LPPL).

EXAMPLE VII

Identification of a functional NES in the capsid protein of a geminivirus. Tomato yellow leaf curl virus (TYLCV) is a constant threat to tomato growers around the world (Cohen et al. 1964). TYLCV is a monopartite geminivirus containing only one genomic circular ssDNA encapsulated by the viral capsid protein (CP)(Davies et al. 1989). Upon infection, TYLCV is imported into the host plant cell nucleus where DNA replication, transcription, and virus assembly presumably take place (Navot et al. 1991). Whereas nuclear import of TYLCV is likely mediated by its NLS-bearing CP (Kunik et al. 1998), the mechanism by which this virus is exported from the nucleus for cell-to-cell movement and spread of infection remains unknown. Here, the pNEA-based nuclear export assay and histidine selection were used to demonstrate that, in addition to its NLS, TYLCV CP contains a NES functional in yeast.

Figure 24:
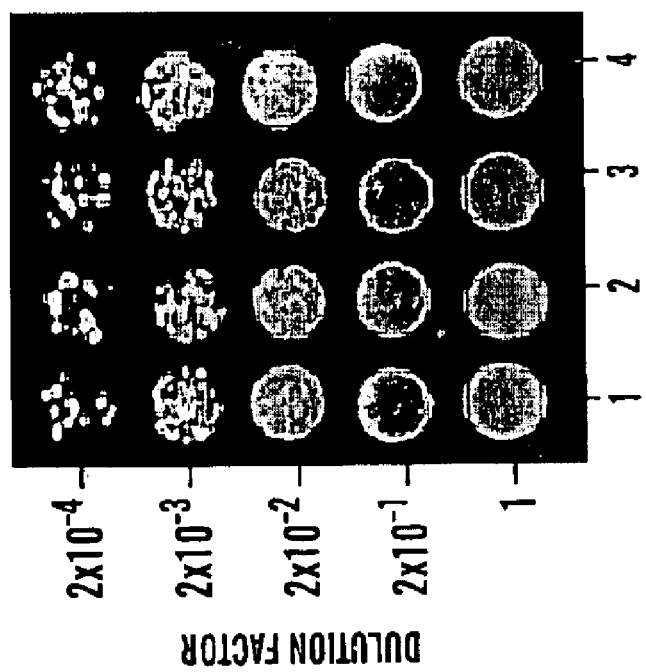
FIG. 24 illustrates the results of the selective reporter gene (HIS3) used to detect nuclear export of the CP of TYLCV (medium deficient for only tryptophan).
Figure 23:
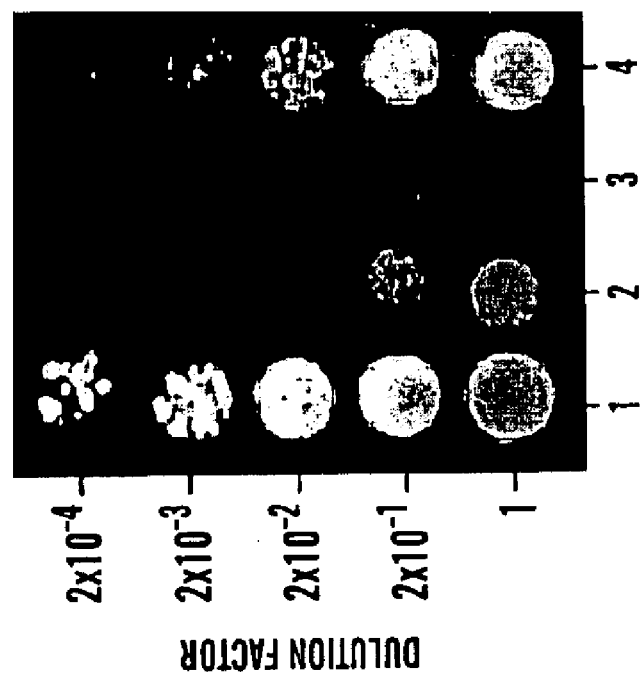
FIG. 23 illustrates the results of the selective reporter gene (HIS3) used to detect nuclear export of the capsid protein (CP) of tomato yellow leaf curl virus (TYLCV) (medium deficient for both tryptophan and histidine)

FIG. 23 shows that, similarly to Rev, a CP fusion substantially decreased histidine prototrophy, indicating reduction in HIS3 gene expression and, by implication, the presence of an active NES within CP. Next, the CP NES was mapped relative to its known NLS sequences which reside at the amino terminus (major NLS) and in the middle part of the protein (augmenting NLS)(Kunik et al. 1998). The CP amino terminus promoted efficient expression of the reporter genes (data not shown), suggesting that the CP NES is located within the deleted part of the protein, i.e. residues 38 to 260. Deletion of amino acid residues from 38 to 113 (CPΔM mutant), on the other hand, did not enhance HIS3 gene expression (FIG. 23). This result indicates that the CP NES is not present in the middle portion of CP; in fact, deletion of the augmenting middle NLS apparently enhanced nuclear export of the mutant protein as compared to the full length CP (FIG. 23). In contrast, removal of the CP carboxy terminus (residues 114 to 260, CPΔC mutant) restored HIS3 expression (FIG. 23), suggesting that the deleted carboxy terminal region contains a functional NES signal. The differences in colony formation on the selective medium reflected changes in the expression of the HIS3 reporter because CP and all its mutants exhibited equal growth in the absence of histidine selection (FIG. 24). Thus, CP likely contains two types of spatially distant targeting signals, amino terminal and middle NLSs and a carboxy terminal NES.

More particularly, FIGS. 23 and 24 show the detection of NES within TYLCV CP. FIG. 23 shows the selection assay by cell growth on minimal medium deficient for both tryptophan and histidine. FIG. 24 shows cell growth on minimal medium deficient for only tryptophan. (1), pNEA alone; (2) pNEACP; (3) pNEACPΔM; (4) pNEACPΔC.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

REFERENCES

Ausubel et al. (1987) in "Current Protocols in Molecular Biology," Greene Publishing-Wiley Interscience, New York.

Ballas and Citovsky (1997) Proc Natl Acad Sci USA 94:10723–10728.

Bardwell et al. (1993) Med Microbiol 8:1177.
Bartel et al. (1993) Biotechniques 14:920.
Bogerd et al. (1993) J Virol 67:5030.
Chakraborty et al. (1992) J Biol Chem 267:17498.
Chein et al. (1991) Proc Natl Acad Sci USA 88:9578.
Citovsky et al. (1988) Science 240:501–504.
Citovsky et al. (1992) Science 256:1803–1805.
Citovsky et al. (1994) Proc Natl Acad Sci USA 91:3210–3214.
Cohen and Harpaz (1964) Entomol Exper Appl 7:155–166.
Dasmahapatra et al. (1992) Proc Natl Acad Sci USA 89:4159.
Davies et al. (1989) Trends Genet 5:77–81.
Dingwall (1991) BioEssays 13:213–218.
Dingwall and Laskey (1991) Trends Biochem Sci 16:478–481.
Dobbelstein et al. (1997) EMBO J. 16:4276–4284.
Durfee et al. (1993) Genes Devel 7:555.
Fields and Song (1989) Nature 340:245.
Garcia-Bustos et al. (1991) Biochim Biophys Acta 1071:83–101.
Germino et al. (1993) Proc Natl Acad Sci USA 90:933.
Goldfarb et al. (1986) Nature 322:641–644.
Guarente (1993) Proc Natl Acad Sci USA 90:1639.
Guralnick et al. (1996) Plant Cell 8:363–373.
Hardy et al. (1992) Genes Devel 6:801.
Hollenberg et al. (1995) Mol Cell Biol 15:3813–3822.
Howard et al. (1992) Cell 68:109–118.
Iwabuchi et al. (1993) Oncogene 8:1693.
Jackson et al. (1993) Mol Cell Biol 13:2899.
Kaiser et al. (1994) "Methods in Yeast Genetics" Cold Spring Harbor Laboratory Press, Cold Spring Harbor, N.Y.
Kalderon et al. (1984) Cell 39:499–509.
Kunik et al. (1998) Plant J 13:393–399.
Lalo et al. (1993) Proc Natl Acad Sci USA 90:5524.
Li and Fields (1993) FASEB J 7:957.
Luban et al. (1993) Cell 73:1067.
Ma and Ptashne (1988) Cell 55:443.
Madura et al. (1993) J Biol Chem 268:12046.
Malim et al. (1989) Cell 58:205–214.
McDonald et al. (1998) Proc Natl Acad Sci USA 95:7457–7462.
Michael et al. (1995) Cell 83:415–422.
Milne and Weaver (1993) Genes Devel 7:1755.
Navot et al. (1991) Virology 185:151–161.
Newmeyer et al. (1988) Cell 52:641–653.
Nigg (1997) Nature 386:779–787.
Ossareh-Nazari et al. (1997) Science 278:141–144.
Pollard and Malim (1998) Annu Rev Microbiol 52:491–532.
Robbins et al. (1991) Cell 64:615–623.
Roberts et al. (1987) Cell 50:465–475.
Sambrook et al. (1989) "Molecular Cloning: A Laboratory Manual," 2d Edition, Cold Spring Harbor Laboratory Press, Cold Spring Harbor, N.Y.
Schlenstedt et al. (1993) J Cell Biol 123:785–798.
Silver and Hunt (1993) Mol Biol Rep 17:155.
Silver et al. (1988) Genes Dev 2:707–717.
Stachel et al. (1985) EMBO J. 4:891–898.
Straudinger et al. (1993) J Biol Chem 268:4608.
Taagepera et al. (1998) Proc Natl Acad Sci USA 95:7457–7462.
Ullman et al. (1997) Cell 90:967–970.
Varagona et al. (1991) Plant Cell 3:105–113.
Vojtek et al. (1993) Cell 74:205.
Yang et al. (1992) Science 257:680.

What is claimed is:

1. A method of determining the presence of a nuclear localization signal in a protein of interest, the method comprising:
   selecting a host cell for use in the method, wherein the host cell contains a nucleus having nucleic acid encoding a reporter gene therein and wherein the host cell has a first level of expression of the reporter gene;
   identifying a DNA binding domain and an activation domain for the reporter gene;
   constructing a chimeric nucleic acid encoding a fusion protein comprising the DNA binding domain, the activation domain, and a protein of interest, wherein elements of the fusion protein other than the protein of interest have no nuclear localization signals;
   introducing the chimeric nucleic acid into the host cell; and
   determining a second level of expression of the reporter gene to determine the presence of a nuclear localization signal in the protein of interest.

2. The method of claim 1 wherein the host cell is a eukaryotic cell.

3. The method of claim 1 wherein the host cell is a yeast cell.

4. The method of claim 1 wherein the reporter gene is a lacZ gene.

5. The method of claim 1 wherein the reporter gene is a selection marker gene.

6. The method of claim 5 wherein the selection marker gene is a HIS3 gene.

7. The method of claim 4 or 6 wherein the DNA binding domain is from a LexA protein.

8. The method of claim 4 or 6 wherein the activation domain is a GAL4 activation domain.

9. The method of claim 1 wherein the chimeric nucleic acid further comprises nucleic acid encoding a promoter to control expression of the fusion protein.

10. The method of claim 9 wherein the promoter is an ADH1 promoter.

11. A recombinant host cell comprising:
    a nucleus having nucleic acid encoding a reporter gene therein; and
    a chimeric nucleic acid encoding a fusion protein, the fusion protein comprising a DNA binding domain for the reporter gene, an activation domain for the reporter gene, and a protein of interest, wherein elements of the fusion protein other than the protein of interest have no nuclear localization signals and wherein the DNA binding domain is from a LexA protein.

12. The recombinant host cell of claim 11 wherein the host cell is a eukaryotic cell.

13. The recombinant host cell of claim 11 wherein the host cell is a yeast cell.

14. The recombinant host cell of claim 11 wherein the reporter gene is a lacZ gene.

15. The recombinant host cell of claim 11 wherein the reporter gene is a selection marker gene.

16. The recombinant host cell of claim 15 wherein the selection marker gene is a HIS3 gene.

17. The recombinant host cell of claim 14 or 16 wherein the activation domain is a GAL4 activation domain.

18. The recombinant host cell of claim 11 wherein the chimeric nucleic acid further comprises nucleic acid encoding a promoter to control expression of the fusion protein.

19. The recombinant host cell of claim 18 wherein the promoter is an ADH1 promoter.

20. A chimeric nucleic acid encoding a fusion protein, the fusion protein comprising a DNA binding domain for a reporter gene, an activation domain for the reporter gene, and a protein of interest, wherein elements of the fusion protein other than the protein of interest have no nuclear localization signals and wherein the DNA binding domain is from a LexA protein.

21. The chimeric nucleic acid of claim 20 wherein the reporter gene is a lacZ gene.

22. The chimeric nucleic acid of claim 21 or 24 wherein the activation domain is a GAL4 activation domain.

23. The chimeric nucleic acid of claim 20 wherein the reporter gene is a selection marker gene.

24. The chimeric nucleic acid of claim 23 wherein the selection marker gene is a HIS3 gene.

25. The chimeric nucleic acid of claim 20 further comprising nucleic acid encoding a promoter to control expression of the fusion protein.

26. The chimeric nucleic acid of claim 25 wherein the promoter is an ADH1 promoter.

27. A vector comprising the chimeric nucleic acid of claim 20.

28. A kit comprising the vector of claim 27.

29. The kit of claim 28 further comprising host cells which contain a nucleus having nucleic acid encoding the reporter gene therein.

30. The kit of claim 29 further comprising a control vector.

31. A nucleic acid molecule encoding a modified LexA protein, wherein the modified LexA protein has no nuclear localization signal.

32. The nucleic acid molecule of claim 31 wherein the nucleic acid molecule has a nucleotide sequence as shown in SEQ ID NO:1.

33. The nucleic acid molecule of claim 31 wherein the nucleic acid molecule encodes an amino acid sequence as shown in SEQ ID NO:2.

34. A modified LexA protein, wherein the modified LexA protein has no nuclear localization signal.

35. The modified LexA protein of claim 34 wherein the protein has an amino acid sequence as shown in SEQ ID NO:2.

* * * * *